(12) United States Patent
Ahmed et al.

(10) Patent No.: US 9,180,175 B2
(45) Date of Patent: Nov. 10, 2015

(54) METHODS OF USE FOR A NATURAL THOMSEN-FRIEDENREICH DISACCHARIDE COMPOUND

(75) Inventors: Hafiz Ahmed, Aldie, VA (US); Prasun Guha, Baltimore, MD (US); Engin Kaptan, Baltimore, MD (US); Gerardo Vasta, Columbia, MD (US); Gargi Bandyopadhyaya, Cockeysville, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 582 days.

(21) Appl. No.: 13/430,938

(22) Filed: Mar. 27, 2012

(65) Prior Publication Data
US 2012/0251580 A1 Oct. 4, 2012

Related U.S. Application Data

(60) Provisional application No. 61/469,891, filed on Mar. 31, 2011.

(51) Int. Cl.
*A01N 37/18* (2006.01)
*A61K 39/00* (2006.01)
*A61K 39/395* (2006.01)

(52) U.S. Cl.
CPC ....... *A61K 39/0011* (2013.01); *A61K 39/39558* (2013.01)

(58) Field of Classification Search
None
See application file for complete search history.

(56) References Cited

U.S. PATENT DOCUMENTS

2010/0297159 A1* 11/2010 Irazoqui et al. ............ 424/185.1

OTHER PUBLICATIONS

Djeu, J. et al., Clusterin and chemoresistance, Adv. Cancer Res., 2009, vol. 105, pp. 77-92.
Al-Mehdi, A.B. et al., Intravascular origin of metastasis from the proliferation of endothelium-attached tumor cells: a new model for metastasis, Nature Medicine, 2000, vol. 6, No. 1, pp. 100-102.
Yu, L.G., The oncofetal Thomsen-Friedenreich carbohydrate antigen in cancer progression, Glycoconj J, 2007, vol. 24, pp. 411-420.
Glinsky, V. et al., The role of Thomsen-Friedenreich antigen in adhesion of human breast and prostate cancer cells to the endothelium, Cancer Res., 2001, vol. 61, pp. 4851-4857.
Zhao, Q. et al., Interaction between circulating galectin-3 and cancer-associated MUC1 enhances tumour cell homotypic aggregation and prevents anoikis, Molecular Cancer, 2010, vol. 9, pp. 154-165.
Shekhar, M. et al., Alterations in galectin-3 expression and distribution correlate with breast cancer progression: functional analysis of galectin-3 in breast epithelial-endothelial interactions, American Journal of Pathology, 2004, vol. 165, No. 6, pp. 1931-1941.

Wu, A. et al., Differential contributions of recognition factors of two plant lectins -*Amaranthus caudatus* lectin and *Arachis hypogea* agglutinin, reacting with Thomsen-Friedenreich disaccharide (Galbeta1-3GalNAcalpha1-Ser/Thr), Biochimie, 2008, vol. 90, pp. 1769-1780.
Ahmed, H. et al., Further characterization and immunochemical studies on the carbohydrate specificity of jackfruit (*Artocarpus integrifolia*) lectin, Journal of Biological Chemistry, 1989, vol. 264, No. 16, pp. 9365-9372.
Ideo, H. et al., Recognition mechanism of galectin-4 for cholesterol 3-sulfate, Journal of Biological Chemistry, 2007, vol. 282, No. 29, pp. 21081-21089.
Nagae, M. et al., Crystal structure of the galectin-9 N-terminal carbohydrate recognition domain from *Mus musculus* reveals the basic mechanism of carbohydrate recognition, Journal of Biological Chemistry, 2006, vol. 281, No. 47, pp. 35884-35893.
Liu, F.T. et al., Galectins as modulators of tumour progression, Nature Reviews Cancer, 2005, vol. 5, pp. 29-41.
Liao, D.I. et al., Structure of S-lectin, a developmentally regulated vertebrate β-galactoside binding protein, Proc. Natl. Acad. Sci. USA, 1994, vol. 91, pp. 1428-1432.
Fukumori, T. et al., Galectin-3 regulates mitochondrial stability and antiapoptotic function in response to anticancer drug in prostate cancer, Cancer Res., 2006, vol. 66, No. 6, pp. 3114-3119.
Nangia-Makker, P. et al., Regulation of tumor progression by extracellular galectin-3, Cancer Microenvironment, 2008, vol. 1, pp. 43-51.
Fukumori, T. et al., CD29 and CD7 mediate galectin-3-induced type II T-cell apoptosis, Cancer Research, 2003, vol. 63, pp. 8302-8311.
Hsu, D. et al., Galectin-3 regulates T-cell functions, Immunological Reviews, 2009, vol. 230, pp. 114-127.
Li, W. et al., CD133+ human pulmonary adenocarcinoma cells induce apoptosis of CD8+T cells by highly expressed galectin-3, Clin. Invest. Med., 2010, vol. 33, pp. E44-53.
Devries, A. et al., Primary structure of freezing point-depressing glycoproteins, Journal of Biological Chemistry, 1971, vol. 246, No. 2, pp. 305-308.
Fletcher, G. et al. Low temperature regulation of antifreeze glycopeptide levels in Atlantic cod (*Gadus morhua*), Can. J. Zool., 1987, vol. 65, pp. 227-233.
Pacts, R. et al., Decreased galectin-3 expression in prostate cancer, Prostate, 2000, vol. 44, pp. 118-123.
Ahmed, H. et al., Evidence of heavy methylation in the galectin-3 promoter in early stages of prostate adenocarcinoma: Development and validation of a methylated marker for early diagnosis of prostate cancer, Translational Oncology, 2009, vol. 2, No. 3, pp. 146-156.
Geng, D. et al., Amplifying TLR-MyD88 signals within tumor-specific T cells enhances antitumor activity to suboptimal levels of weakly immunogenic tumor antigens, Cancer Res., 2010, vol. 70, No. 19, pp. 7442-7454.

(Continued)

*Primary Examiner* — Laura B Goddard
*Assistant Examiner* — Meera Natarajan
(74) *Attorney, Agent, or Firm* — Wenderoth, Lind & Ponack LLP

(57) ABSTRACT

A Thomsen-Friedenreich disaccharide-containing glycopeptide purified from cod fish of approximately 100 kDa (designated TFD$_{100}$) and methods of using the same in the suppression of cancer metastasis is disclosed.

4 Claims, 11 Drawing Sheets

(56) References Cited

OTHER PUBLICATIONS

Massa, S. et al., L-29, an endogenous lectin, binds to glycoconjugate ligands with positive cooperativity, Biochemistry, 1993, vol. 32, pp. 260-267.

Ketis, N. et al., Positive cooperativity in a (dissected) lectin-membrane glycoprotein binding event, Proc. Natl. Acad. Sci. USA, 1980, vol. 77, No. 7, pp. 3788-3790.

Carmeliet, P. et al., Angiogenesis in cancer and other diseases, Nature, 2000, vol. 407, pp. 249-257.

Markowska, A. et al., Galectin-3 is an important mediator of VEGF- and bFGF-mediated angiogenic response, J. Exp. Med., 2010, vol. 207, No. 9, pp. 1981-1993.

Nangia-Makker, P. et al., Galectin-3 induces endothelial cell morphogenesis and angiogenesis, American Journal of Pathology, 2000, vol. 156, No. 3, pp. 899-909.

Springer, G., Immunoreactive T and Tn epitopes in cancer diagnosis, prognosis, and immunotherapy, J. Mol. Med., 1997, vol. 75, pp. 594-602.

Almogren, A. et al., Anti-Thomsen-Friedenreich-Ag (anti-Tf-Ag) potential for cancer therapy, Frontiers in Bioscience (Schol. Ed), 2012, vol. 4, pp. 840-863.

Lawrence, M. et al., Leukocytes roll on a selectin at physiologic flow rates: distinction from and prerequisite for adhesion through integrins, Cell, 1991, vol. 65, pp. 859-873.

Peng, W. et al., Tumor-associated galectin-3 modulates the function of tumor-reactive T cells, Cancer Res., 2008, vol. 68, pp. 7228-7236.

Zou, W., Immunosuppressive networks in the tumour environment and their therapeutic relevance, Nature Reviews Cancer, 2005, vol. 5, pp. 263-274.

Yu, L. et al., Galectin-3 interaction with Thomsen-Friedenreich disaccharide on cancer-associated MUC1 causes increased cancer cell endothelial adhesion, Journal of Biological Chemistry, 2007, vol. 282, No. 1, pp. 773-781.

Dubois, M. et al., Colorimetric method for determination of sugar, Nature, 1951, vol. 168, p. 167.

Laemmli, U.K. et al., Maturation of the head of bacteriophage T4. I. DNA packaging events, J. Mol. Biol., 1973, vol. 80, pp. 575-599.

Ahmed, H. et al., The primary structure and carbohydrate specificity of a β-galactosyl-binding lectin from toad (*Bufoarenarum hensel*) ovary reveal closer similarities to the mammalian galectin-1 than to the galectin from the clawed frog *Xenopus laevis*, Journal of Biological Chemistry, 1996, vol. 271, No. 51, pp. 33083-33094.

Alimirah, F. et al., DU-145 and PC-3 human prostate cancer cell lines express androgen receptor: implications for the androgen receptor functions and regulation, FEBS Letters, 2006, vol. 580, pp. 2294-2300.

Pulukuri, S. et al., RNA interference-directed knockdown of urokinase plasminogen activator and urokinase plasminogen activator receptor inhibits prostate cancer cell invasion, survival, and tumorigenicity in Vivo, Journal of Biological Chemistry, 2005, vol. 280, No. 43, pp. 36529-36540.

\* cited by examiner

METHODS OF USE FOR A NATURAL THOMSEN-FRIEDENREICH DISACCHARIDE COMPOUND

CROSS-REFERENCE TO RELATED APPLICATIONS

The present application claims priority to U.S. provisional application No. 61/469,891, filed Mar. 31, 2011, the entire disclosure of which is herein incorporated by reference.

STATEMENT OF FEDERALLY SPONSORED RESEARCH AND DEVELOPMENT

This invention was made with government support under Grant Number CA133935 awarded by the National Institutes of Health, and Grant Number W81XWH-07-1-0565 awarded by the U.S. Army MRMC. The government has certain rights in the invention.

TECHNICAL FIELD

The invention relates to a Thomsen-Friedenreich disaccharide-containing glycopeptide purified from cod fish of approximately 100 kDa (designated $TFD_{100}$) and methods of using the same in the suppression of cancer metastasis.

BACKGROUND OF INVENTION

Prostate cancer (PCa) is a leading cause of cancer death of men in the United States and Europe. Androgen therapy is the treatment of choice in men with metastatic disease. However, most patients develop androgen-insensitivity and chemoresistance, and die within a few years (1). Therefore, alternative strategies for prevention and treatment of PCa metastasis are urgently needed.

Cancer metastasis involves a series of steps such as angiogenesis, detachment of a metastatic cell from the primary tumor, intravasation, evasion of host defense, arrest at a distant site, attachment, extravasation, dormant survival, and establishment of new growth. During extravasation, cancer cells bind to endothelial cells through protein-carbohydrate interactions and penetrate through the endothelium and basement membrane (2). Thus, tumor-endothelial interaction and angiogenesis are considered key steps prior to cancer metastasis (2). Disruption of such interactions (5) may effectively prevent metastasis.

It has been demonstrated that Thomsen-Friedenreich (TF) antigen (Galβ1-3GalNAcα1-Ser/Thr) is expressed by carcinomas (3). The TF antigen (also known as CD176) is present in the core I structure of mucin-type O-linked glycan. It is generally masked by sialic acid in normal cells, but it is exposed or non-sialylated in malignant and premalignant epithelia (3). Increased surface expression of TF antigen is associated with poorer prognosis in ovarian, lung, gastric, colon, breast, and prostate cancers, implying that TF antigen is involved in cancer progression and metastasis (3).

It has been shown that endothelial cell-expressed galectin gal3 participates in docking of cancer cells including breast and prostate cancers by specifically interacting with cancer cell-associated TF disaccharide (TFD, Galβ1,3GalNAc) (4). It has further been shown that cell surface TFD mediates homotypic cell adhesion by binding to circulating gal3 (5), although other interactions could be involved. The significance of gal3-TFD interactions in mediating homotypic and heterotypic cell-cell interactions was also demonstrated by using three-dimensional co-cultures of endothelial and epithelial cells (6). Intracellular gal3 enhances mitochondrial stability and inhibits apoptosis in PCa cells in presence of certain chemotherapeutics (13). Other studies have shown that extracellular gal3 is involved in tumor cell adhesion (14). In addition to both intracellular and extracellular functions, tumor-secreted gal3 induces apoptosis of infiltrating T cells, thus acting as double-edged sword to evade immune surveillance during tumor progression (15-17).

Although several plant lectins such as peanut agglutinin (PNA), jack fruit lectin (jacalin) and *Amaranthus caudatus* lectin can bind to TFD (7, 8), only three mammalian lectins (gal3, gal4, and gal9) are known to interact with TFD (9, 10). These galectins can also bind N-acetyllactosamine and other N-glycans (7, 8), which may be relevant in cancer progression (11). The basis for the variable binding profiles of these galectins has been explained by their 3-D structures (9, 10, 12). Both gal4 and gal9 seem to have some roles in cancer progression (11), but it is not known if they participate through the TFD binding.

Therapeutic compositions and methods of suppressing cancer metastasis might be developed based on the interactions between TFD and galectins such as gal3.

BRIEF SUMMARY OF INVENTION

In order to explore a possible anti-tumor effect of a naturally-occurring TFD-containing compound that could act as an antagonist of lectins such as gal3 and that can be taken as food supplement, a TFD-containing glycopeptide (designated $TFD_{100}$) has been purified from the Pacific cod (*Gadus macrocephalus*) by employing affinity chromatography and gel permeation chromatography. As shown herein, $TFD_{100}$ inhibited adhesion of cells of the prostate cancer cell line PC3 to endothelial cells in vitro, an also inhibited angiogenesis and gal3-mediated T-cell apoptosis. The glycopeptide was further found to prevent PC3-induced metastasis in mice. Thus, an edible TFD-containing bioactive compound having applications in cancer therapeutics, particularly suppressing cancer metastasis, such as prostate cancer metastasis, has been developed and is described herein.

The invention thus relates to methods based on reducing gal3 activity, both in vitro and in vivo.

In a first embodiment of the invention, a method of reducing gal3 activity in a subject is provided, which comprises administering an effective amount of a TFD-containing glycopeptide to a subject in need thereof, thereby reducing gal3 activity in a subject.

In a second embodiment of the invention, a method of inhibiting gal3-TFD binding in a subject is provided, which comprises administering an effective amount of a TFD-containing glycopeptide to a subject in need thereof, thereby inhibiting gal3-TFD binding in a subject. In certain aspects, gal3 and TFD are cell-surface localized and on different cells. In other aspects, gal 3 is soluble and TFD is cell-surface localized.

In a third embodiment of the invention, a method of inhibiting tumor-endothelial cell interaction in a subject is provided, which comprises administering an effective amount of a TFD-containing glycopeptide to a subject in need thereof, thereby inhibiting tumor-endothelial cell interaction in a subject. In certain aspects, the interaction is binding of tumor cells to endothelial cells.

In a fourth embodiment of the invention, a method of suppressing metastasis in a subject is provided, which comprises administering an effective amount of a TFD-containing glycopeptide to a subject having cancer, thereby suppressing metastasis in a subject.

In a fifth embodiment of the invention, a method of suppressing angiogenesis in a subject is provided, which comprises administering an effective amount of a TFD-containing glycopeptide to a subject in need thereof, thereby suppressing angiogenesis in a subject. In certain aspects, angiogenesis of a tumor is suppressed.

In a sixth embodiment of the invention, a method of suppressing gal3-mediated T cell apoptosis in a subject is provided, which comprises administering an effective amount of a TFD-containing glycopeptide to a subject in need thereof, thereby suppressing gal3-mediated T cell apoptosis in a subject. In certain aspects, the T cells are CD8$^+$ T cells, including antigen-activated CD8$^+$ T cells.

In a seventh embodiment of the invention, a method of suppressing tumor-induced T cell apoptosis in a subject is provided, which comprises administering an effective amount of a TFD-containing glycopeptide to a subject having a tumor, thereby suppressing tumor-induced T cell apoptosis in a subject. In certain aspects, the T cells are CD8$^+$ T cells, including antigen-activated CD8$^+$ T cells. In further aspects, cells of the tumor express gal3, such as cell-surface expressed gal3.

In an eighth embodiment of the invention, a method of protecting CD8$^+$ activity in a subject is provided, which comprises administering an effective amount of a TFD-containing glycopeptide to a subject being treated for cancer, thereby protecting CD8$^+$ activity in a subject.

In a ninth embodiment of the invention, a method of suppressing gal3-mediated homotypic cell aggregation in a subject is provided, which comprises administering an effective amount of a TFD-containing glycopeptide to a subject in need thereof, thereby suppressing gal3-mediated homotypic cell aggregation in a subject. In certain aspects, the homotypic cells are cancer cells, such as prostate cancer cells.

The present invention also relates to methods of inhibiting gal4-TFD interactions and gal9N-TFD interactions, both in vitro and in vivo. Additional embodiments of the invention include methods of inhibiting gal4-TFD binding in a subject, which comprises administering an effective amount of a TFD-containing glycopeptide to a subject, thereby inhibiting gal4-TFD binding in a subject, and methods of inhibiting gal9N-TFD binding in a subject, which comprises administering an effective amount of a TFD-containing glycopeptide to a subject, thereby inhibiting gal9N-TFD binding in a subject.

In each of the embodiments and aspects of the invention, the TFD-containing glycopeptide may be TFD$_{100}$.

In each of the embodiments and aspects of the invention, the subject may be a subject having cancer or a subject at risk for developing cancer. The cancer may be benign, pre-metastatic or metastatic. The cancer may be, for example, but not limited to, prostate cancer.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 1A: Separation of affinity purified TFD-containing glycopeptides on a Superdex 75 10/300 GL column calibrated with bovine serum albumin (dimer 132 kDa and monomer 66 kDa), chymotripsinogen (25 kDa), ribonuclease A (14 kDa), and aprotinin (6.5 kDa). FIG. 1B: SDS-PAGE under reducing condition on 4-12% Bis-Tris gels followed by silver staining, (i) Crude AFGP (10 μg), (ii) TFD$_{100}$ (5 μg), and (iii) Western blot of TFD$_{100}$ (5 μg) followed by PNA binding. FIG. 1C: Inhibition of gal3 binding to asialofetuin. FIGS. 1D, E: Surface plasmon resonance assay on Biacore. The TFD was measured from 31 μM to 1000 μM, and the K$_d$ was determined to be 6.36$^{e-11}$ (M) or 636 μM. TFD$_{100}$ was measured from 0.312 nM to 10 nM and the K$_d$ was determined to be 9.677$^{e-11}$ (M) or 97 μM. The full kinetic analysis results are: ka=3.105E+6 (1/Ms); kd=3.004E-4 (1/s); K$_d$=9.677$^{e-11}$ (M); Rmax=31 (RU); Tc=2.26E+18; Chi$^2$=0.112 (RU$^2$); U-value=2.

FIG. 2G: Quantitation of angiogenesis as measured by number of capillary tube branch point. The data are shown as the means±S.D. from three determinations. ***, p<0.001; ###, p<0.001, ANOVA.

FIG. 3A: BPH; FIG. 3B: stage I (T1N0Mx); FIG. 3C: stage II (T2N0Mx); FIG. 3D: stage III (T3N0Mx); FIG. 3E: stage IV (T4N1Mx). FIG. 3F-J. Expression of TFD as determined by binding with PNA-FITC. Representative results; magnification, ×400. FIG. 3F: Normal; FIG. 3G: stage I (T1N0Mx); FIG. 3H: stage II (T2N0Mx); FIG. 3I: stage III (T3N0Mx); FIG. 3J: stage IV (T4N1Mx).

In FIG. 4A: black (left peak), unstained cells, mean fluorescence unit 205; blue (right peak), with gal3 Ab, mfu 25851; and red (center peak), with pre-immune IgG, mfu 759. In FIG. 4C: red (left peak), unstained cells, mfu 97; blue (right peak), with gal3 Ab, mfu 296; and green (center peak), cells stained with pre-immune IgG, mfu 95. Expression of TFD in PC3 (FIG. 4B) and HUVEC (FIG. 4D) cells. In FIG. 4B: black (left peak), unstained cells, mfu 183; blue (right peak), with PNA-FITC, mfu 59320; and red (center peak), with PNA-FITC plus lactose, mfu 8386. In FIG. 4D: red, unstained cells, mfu 97; blue, with PNA-FITC, mfu 95; and green, with PNA-FITC plus lactose, mfu 97. FIG. 4E: Glycan differentiation analysis of PC3 (i) and HUVEC (ii) cell extract. FIG. 4E (iii): Dot blot of HUVEC extract and others stained with Coomassie showing protein/glycoprotein load. FIG. 4F: Quantitation of bound PC3 cells pre-treated with various reagents on HUVEC. FIG. 4G: Quantitation of bound PC3 cells on HUVEC pre-treated with various reagents. FIG. 4H: PC3 cell adhesion to HUVEC in the presence of gal3 siRNA and TFD$_{100}$ (3.5 nM). All data (FIGS. 4F-H) are shown as the means±S.D. from three determinations. **, p<0.01, ANOVA.

FIGS. 5A, E: MOLT-4 alone; FIGS. 5B, F: with gal3 (5 μM); FIGS. 5C, G: with gal3 plus TFD$_{100}$ (3.5 nM); FIGS. 5D, H: with gal3 plus lactose (50 μM); FIG. 5I: Preparation of pmel T cells; FIG. 5J: Gating of non-activated pmel T cells; FIG. 5K: pmel T cells alone; FIG. 5L: with gal3 (15 μM); FIG. 5M: Gating of activated pmel T cells; FIG. 5N: pmel T cells alone; FIG. 5O: with gal3 (5 μM); FIG. 5P: with gal3 plus TFD$_{100}$ (3.5 nM); FIG. 5Q: Western blot of normal and prostate cancer patient sera P17 (stage III, GS 4+5) and P19 (stage III, GS 4+4) showing gal3; FIG. 5R: activated pmel T cells with normal serum; FIG. 5S: with P17; FIG. 5T: with P17 plus TFD$_{100}$ (3.5 nM); FIG. 5U: Expression of gal3 on B16 melanoma cell surface (Red (left peak), unstained cells, mean fluorescence unit 214; green (right peak), with gal3 Ab, mfu 2832; and blue (center peak), with pre-immune IgG, mfu 1005; FIG. 5V: B16 cell-associated apoptosis of activated pmel T cells; FIG. 5W: same with 3.5 nM TFD$_{100}$; FIG. 5X: same with gal3 siRNA. FIG. 5Y: Quantitation of apoptosis of activated pmel T cells; and FIG. 5Z: Quantitation of B16-mediated apoptosis of activated pmel T cells. In all cases, apoptosis was assessed by annexin V binding.

FIG. 6A (i): Glow scale of luciferase-expressing PC3 cells injected into the tail vein of nude mice show metastases in the lower abdomen. FIG. 6B: Inhibition of lung photon flux with TFD$_{100}$. FIG. 6C: Inhibition of total body photon flux with TFD$_{100}$.

FIG. 7A: Glycan analysis. Positive reaction with GNA (*Galanthus nivalis* agglutinin) indicates mannose, terminally linked. Positive reaction with SNA (*Sambucus nigra* agglutinin) indicates sialic acid, terminally linked (2-6) to galactose (SAα-2,6Gal). Positive reaction with MAA (*Maackia amurensis* agglutinin) indicates SAα-2,3Gal. Positive reaction with PNA (peanut agglutinin) indicates Galβ1,3GalNAc. Positive reaction with DSA (*Datura strammonium* agglutinin) indicates Galβ1,4GlcNAc. FIG. 7B: Inhibition of gal3 binding to asialofetuin. Each compound was tested in triplicate to inhibit gal3 binding to asialofetuin in 96-well plate as described in Materials and Methods.

FIG. 10A: Gal3-mediated apoptosis of Jurkat cells and their inhibition with 3.5 nM TFD$_{100}$; FIG. 10B: Gal3 dose dependent apoptosis of Jurkat cells. FIG. 10C, G: control CD8+ T cells; FIG. 10D, H: gal3 (5 μM) mediated apoptosis; FIGS. 10E, I: inhibition of gal3-mediated apoptosis with TFD$_{100}$ (3.5 nM); FIGS. 10F, J: inhibition of gal3-mediated apoptosis with lactose (50 μM).

DETAILED DESCRIPTION OF THE INVENTION

I. Definitions

Figure 1:
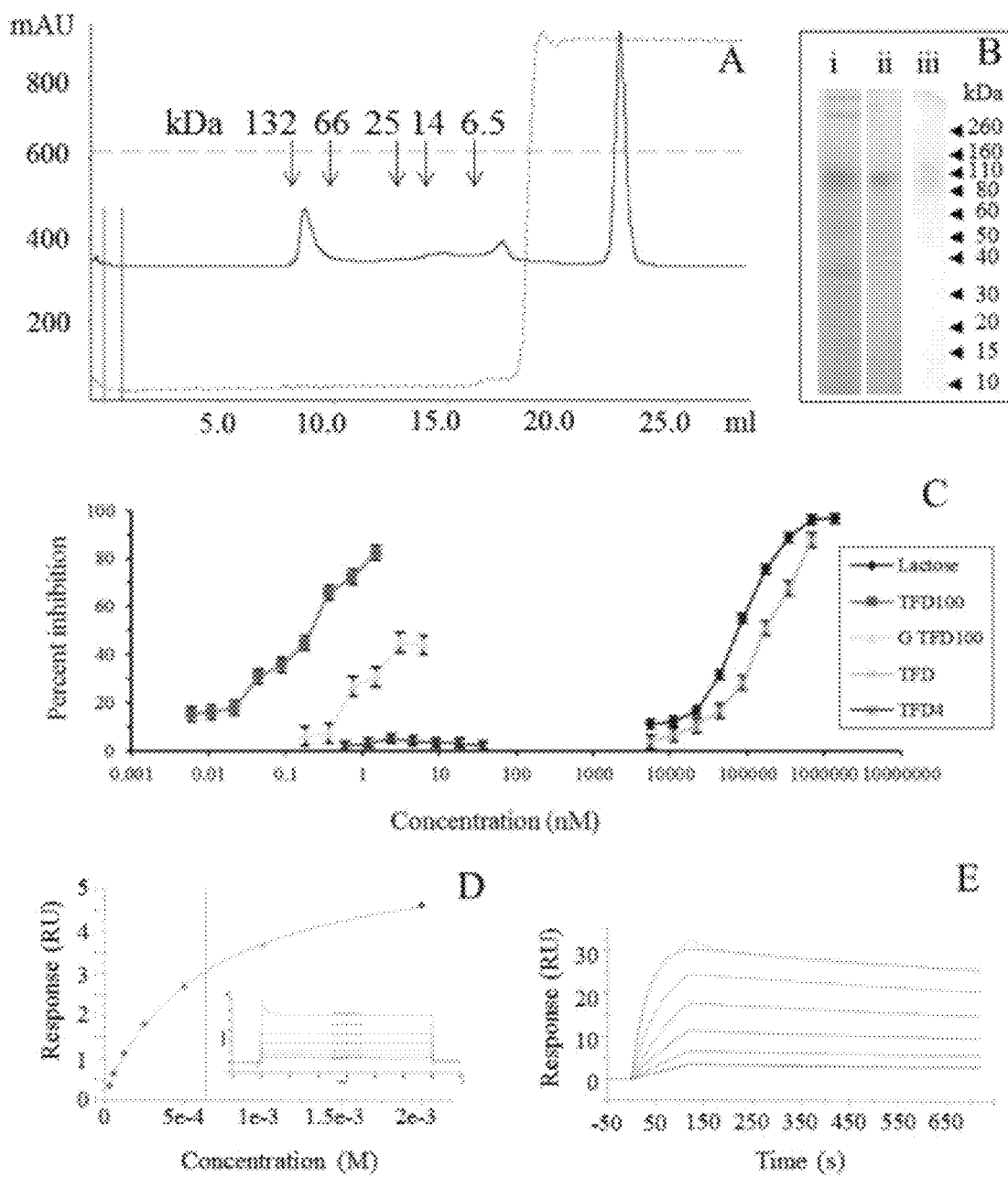
FIG. 1. Purification and characterization of TFD$_{100}$.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, "an effective amount of" is an amount of a TFD-containing glycopeptide of the present invention, whether in the context of an edible formulation or a pharmaceutical formulation, which is sufficient to bring about or achieve a stated goal. For example, an effective amount of a TFD-containing glycopeptide for reducing gal3 activity comprises an amount of a TFD-containing glycopeptide sufficient to inhibit gal3 activity.

II. The Present Invention

Androgen-insensitivity and development of chemoresistance eventually promote metastasis in most PCa patients (1). Therefore alternative strategies for prevention and treatment of PCa metastasis are urgently needed. As tumor-endothelial cell interactions are considered a key step prior to cancer metastasis (2), disruption of such cell:cell interactions, may be an effective strategy for preventing metastasis. Herein, it is demonstrated that galectin-3 (gal3) is involved in the promotion of angiogenesis and tumor-endothelial cell interactions, which can be disrupted with nanomolar quantities of TFD$_{100}$ (a natural TFD-containing glycopeptide of 100 kDa) purified from edible cod fish. TFD$_{100}$ was found very active (in picomolar range) in blocking gal3 binding in both solid phase and surface plasmon resonance assays.

The present invention is therefore directed to methods of reducing gal3 activity which comprise contacting gal3 with an effective amount of a TFD-containing glycopeptide, such as TFD$_{100}$. These methods may be practiced in vitro, such as in screening studies on potential agonists or antagonists of gal3, as well as in vivo, such as in methods of treating, reducing and/or suppressing cancer metastasis, including, but not limited to, those methods described herein that are part of the present invention.

The TFD-containing glycopeptides of the present invention are characterized by the presence of several repeats of a tripeptide of alanine-alanine-threonine in which the last residue is glycosidically-linked to TFD (18). Such glycopeptides include TFD$_{100}$. TFD$_{100}$ is a 100 kDa TFD-containing glycopeptide that may be isolated from isolated from the Pacific cod (*Gadus macrocephalus*) and northern cod (Atlantic cod (*Gadus morhua*); Greenland cod (*Gadus ogac*), as well as Antarctic notothenioids (*Trematomus nicolai*) (18, 19). TFD$_{100}$ is thought to contain several repeats of the tripeptide, which in turn holds multiple TFD. It is known that multiple receptors can enhance binding with many lectins and also with gal3 (23) to a level far greater than the stoichiometric ratio, a phenomenon called "positive co-operativity" (24).

Particular embodiments of the invention include a first embodiment where methods of reducing gal3 activity are provided. For example, the embodiment includes a method of reducing gal3 activity in a subject, comprising administering an effective amount of a TFD-containing glycopeptide to a subject in need thereof, thereby reducing gal3 activity in a subject. In certain aspects, the TFD-containing glycopeptide is $TFD_{100}$.

A related and second embodiment of the invention includes methods of inhibiting gal3-TFD binding. For example, the embodiment includes a method of inhibiting gal3-TFD binding in a subject comprising administering an effective amount of a TFD-containing glycopeptide to a subject in need thereof, thereby inhibiting gal3-TFD binding in a subject. In certain aspects, gal3 and TFD are cell-surface localized and on different cells. In other aspects, gal 3 is soluble and TFD is cell-surface localized. In certain aspects, the TFD-containing glycopeptide is $TFD_{100}$.

Recent studies demonstrate that hematogeneous cancer metastases originate from intravascular growth of endothelium-attached cells highlighting the key role of tumor-endothelial cell interactions in cancer metastasis (2). In the adhesion of tumor cells to the vasculatory endothelium, a broad array of adhesion molecules, such as carbohydrates, lectins, cadherins, and integrins participate at distinct stages in a multistep binding process (4, 30). In an elegant study, Glinsky et al. (4) demonstrated that TF antigen present on the tumor cells caused gal3 mobilization and clustering on the endothelial surface prior to binding. As demonstrated herein, a TF antigen is strongly expressed in stage II and III prostate tumor tissues (see FIG. 3H,I) supporting this hypothesis. It is further shown herein that multiple receptors such as gal3, TF antigen, integrin, MUC1, and VEGFR1 participate in the adhesion of PC-3 cells to HUVECs. PC3 is a human prostate cancer cell line derived from an advanced, androgen-independent bone metastasis-metastasized prostate cancer. PC3 cells have high metastatic potential (41, 42). The 33-45% inhibition of PC-3-HUVEC interaction observed by nanomolar $TFD_{100}$ is likely directed to gal3 interaction. However, it is possible that gal4 and gal9 also have affinity for $TFD_{100}$ and so $TFD_{100}$ may also inhibit other galectin-mediated tumor-endothelial cell interactions. $TFD_{100}$ also inhibited MDA MB231-HUVEC interactions, suggesting that $TFD_{100}$ may have application in other cancers. Therefore, in a third embodiment the present invention provides methods of inhibiting tumor-endothelial cell interaction. For example, the embodiment includes a method of inhibiting tumor-endothelial cell interaction in a subject comprising administering an effective amount of a TFD-containing glycopeptide to a subject in need thereof, thereby inhibiting tumor-endothelial cell interaction in a subject. In certain aspects, the interaction is binding of tumor cells to endothelial cells. In other aspects, the interaction is binding of endothelial cells to tumor cells. In certain aspects, the TFD-containing glycopeptide is $TFD_{100}$.

As gal3 participates in many steps of metastasis, $TFD_{100}$ may exert a 'multi-pronged' attack on gal3-mediated tumorigenesis. As gal3-TFD interaction is common in most epithelial cancers, high affinity $TFD_{100}$ will have applications in the suppression of metastases of many cancers including prostate cancer. Indeed, as shown herein in nude mice, picomole quantity of $TFD_{100}$ inhibited PC3-induced metastasis. Thus, in a fourth embodiment of the invention, methods of suppressing metastasis are provided. For example, the embodiment includes a method of suppressing metastasis in a subject comprising administering an effective amount of a TFD-containing glycopeptide to a subject having cancer, thereby suppressing metastasis in a subject. In certain aspects, the TFD-containing glycopeptide is $TFD_{100}$.

Angiogenesis, the formation of new blood vessels from preexisting vasculature, is a key factor for not only normal homeostasis, but also in the pathogenesis of several diseases, including cancer (25). Recent studies suggest that gal3 is involved in the promotion of angiogenesis through VEGF and bFGF (26). αvβ3 Integrin has also been demonstrated as a major gal3-binding glycoprotein, which is activated in a carbohydrate-dependent manner (26). Binding assays predict two gal3 receptors on HUVEC with nanomolar affinity ($K_d$=0.537×10$^{-9}$ and 7.161×10$^{-9}$), of which integrin may be one ligand (27). As reported herein, natural $TFD_{100}$ with picomolar affinity to gal3 demonstrated in vitro inhibition of angiogenesis. $TFD_{100}$ may interfere with in vivo gal3-integrin interaction (in the range of nanomolar) resulting in the reduction or blocking of in vivo angiogenesis. Therefore, in a fifth embodiment of the invention, methods of suppressing angiogenesis in a subject are provided. For example, the embodiment includes a method of suppressing angiogenesis in a subject comprising administering an effective amount of a TFD-containing glycopeptide to a subject in need thereof, thereby suppressing angiogenesis in a subject. In certain aspects, angiogenesis of a tumor is suppressed. In certain aspects, the TFD-containing glycopeptide is $TFD_{100}$.

Figure 5:
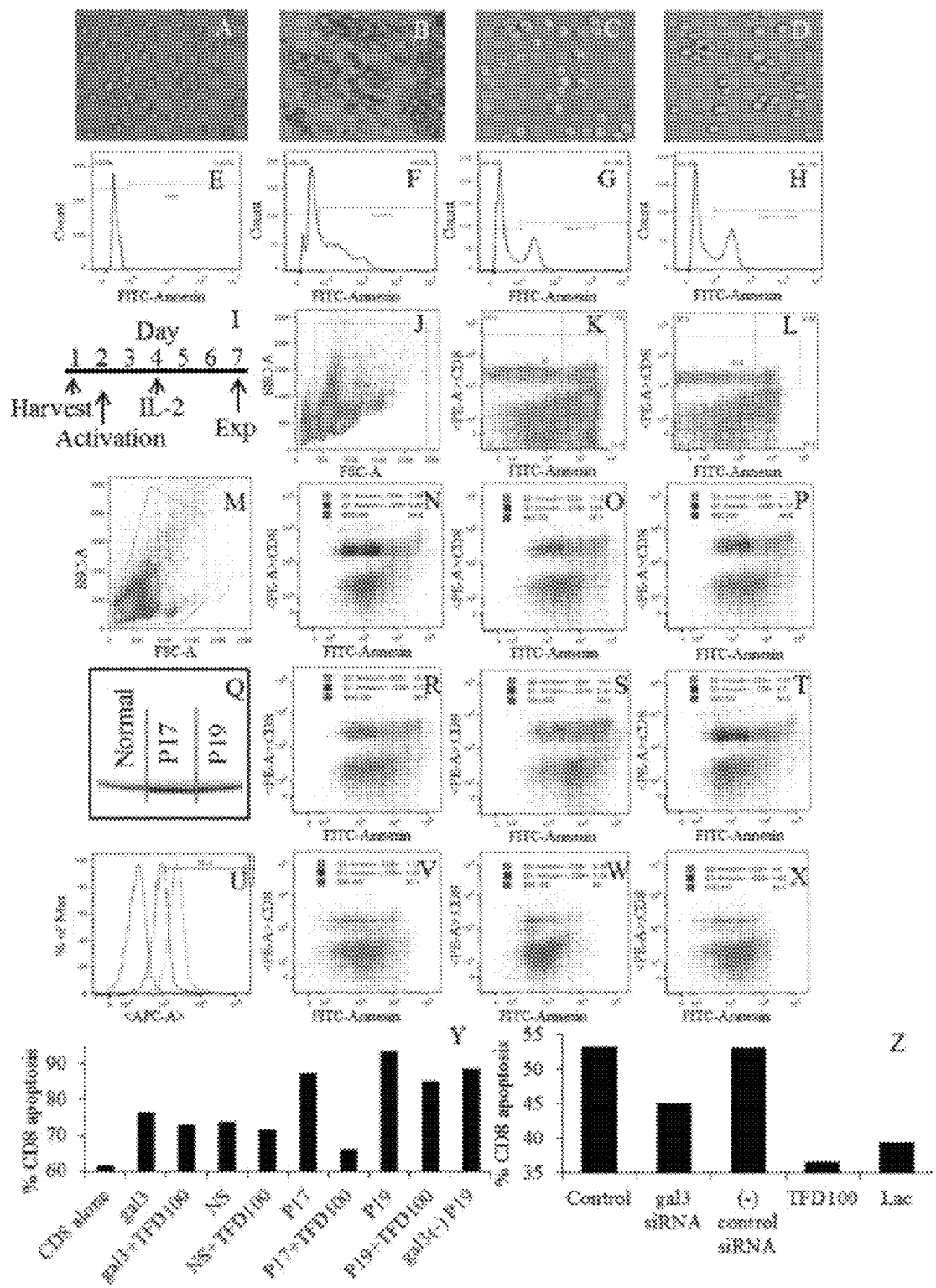
FIG. 5. Apoptosis of T cells: MOLT-4 (FIGS. 5A-H), non-activated (FIGS. 5J-L), and activated transgenic CD90.1 CD8+ (pmel) cells (FIGS. 5M-P, R-T, V-Z).

Tumor-associated galectins such as gal1 and gal3 contribute to tumor immune escape by reducing the function of tumor-reactive T cells (15-17). Particularly, a high dose of gal3 treatment abrogates the efficacy of tumor-reactive T cells and promotes tumor growth in a mouse tumor model (31). Cell surface glycoproteins such as CD29, CD7, CD95, CD98, and T-cell receptor (TCR) have been shown to associate with gal3, which triggers the activation of an intracellular apoptotic signaling cascade followed by mitochondrial cytochrome c release and activation of caspase-3 (15). Moreover, gal3 is shown in the dose dependent cell death of Jurkat with about 8% of cells dying (measured by WST-1 stain) at 10 nM gal3, which is within the observed concentration of gal3 (0.2-1.0 µg/ml equivalent to 6.6-33 nM) in sera of patients with metastatic cancers including prostate cancer (33). Reduction of apoptosis by gal3-depleted patient serum further corroborates the participation of serum gal3 in the apoptotic induction of T cells. As demonstrated herein, gal3-mediated induction of apoptosis of MOLT-4, Jurkat, and CD8+ T cells can be inhibited by nanomolar concentration of $TFD_{100}$ (see FIG. 5). Moreover, murine B16 melanoma induction of apoptosis of tumor-specific CD8 T cells (pmel T cells) was inhibited by $TFD_{100}$. $TFD_{100}$ thus protects antitumor immune responses and in a sixth embodiment of the invention, methods of suppressing gal3-mediated T cell apoptosis are provided. For example, the embodiment includes a method of suppressing gal3-mediated T cell apoptosis in a subject comprising administering an effective amount of a TFD-containing glycopeptide to a subject in need thereof, thereby suppressing gal3-mediated T cell apoptosis in a subject. In certain aspects, the T cells are CD8+ T cells, including antigen-activated CD8+ T cells. In certain aspects, the TFD-containing glycopeptide is $TFD_{100}$. In a related and seventh embodiment, methods of suppressing tumor-induced T cell apoptosis are provided. For example, this embodiment includes a method of suppressing tumor-induced T cell apoptosis in a subject comprising administering an effective amount of a TFD-containing glycopeptide to a subject having a tumor, thereby suppressing tumor-induced T cell apoptosis in a subject. In certain aspects, the T cells are CD8+ T cells, including antigen-activated CD8+ T cells. In further aspects, cells of the tumor express gal3, such as cell-surface expressed gal3. In certain aspects, the TFD-containing glycopeptide is $TFD_{100}$.

The protective effect of $TFD_{100}$ on cytotoxic T cells suggests that the $TFD_{100}$ can also be used as a protective adjuvant in conjunction administration of cancer drugs. In an eighth embodiment of the invention, methods of protecting $CD8^+$ activity are provided. For example, this embodiment includes a method of protecting $CD8^+$ activity in a subject comprising administering an effective amount of a TFD-containing glycopeptide to a subject being treated for cancer, thereby protecting $CD8^+$ activity in a subject. In certain aspects, the TFD-containing glycopeptide is $TFD_{100}$.

In a ninth embodiment of the invention, a method of suppressing gal3-mediated homotypic cell aggregation in a subject is provided, which comprises administering an effective amount of a TFD-containing glycopeptide to a subject in need thereof, thereby suppressing gal3-mediated homotypic cell aggregation in a subject. In certain aspects, the homotypic cells are cancer cells, such as prostate cancer cells. In certain aspects, the TFD-containing glycopeptide is $TFD_{100}$.

Because the TFD-containing glycopeptides, such as $TFD_{100}$, are also shown to bind to the galectins gal4 and gal9N, the present invention is also directed to methods for reducing gal4 activity and methods for reducing gal9N activity, both in vitro and in vivo. The present invention also relates to methods of inhibiting gal4-TFD interactions and gal9N-TFD interactions, both in vitro and in vivo. Additional embodiments of the invention include methods of reducing gal4 activity in a subject, which comprises administering an effective amount of a TFD-containing glycopeptide to a subject, thereby reducing gal4 activity in a subject, and methods of reducing gal9N activity in a subject, which comprises administering an effective amount of a TFD-containing glycopeptide to a subject, thereby reducing gal9N activity in a subject. Further embodiments of the invention include methods of inhibiting gal4-TFD binding in a subject, which comprises administering an effective amount of a TFD-containing glycopeptide to a subject, thereby inhibiting gal4-TFD binding in a subject, and methods of inhibiting gal9N-TFD binding in a subject, which comprises administering an effective amount of a TFD-containing glycopeptide to a subject, thereby inhibiting gal9N-TFD binding in a subject.

III. Formulations and Doses

TFD-containing glycopeptides of the present invention, such as $TFD_{100}$, may be formulated for administration to a subject as an edible formulation. The glycoproteins may be also formulated as a pharmaceutical formulation, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of pharmaceutical formulations can be used to effect such administration. In preferred aspects of each of the embodiments on the invention, TFD-containing glycopeptides are administered to the subject as an edible formulation or an i.p. pharmaceutical formulation.

TFD-containing glycopeptide formulations may be comprised of one or more excipients, carriers, and/or diluents. Excipients included in the formulations have different purposes depending, for example, on the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, lubricating agents (such as talc or silica, and fats, such as vegetable stearin, magnesium stearate or stearic acid), emulsifiers, suspending or viscosity agents, inert diluents, fillers (such as cellulose, dibasic calcium phosphate, vegetable fats and oils, lactose, sucrose, glucose, mannitol, sorbitol, calcium carbonate, and magnesium stearate), disintegrating agents (such as crosslinked polyvinyl pyrrolidone, sodium starch glycolate, cross-linked sodium carboxymethyl cellulose), binding agents (such as starches, gelatin, cellulose, methyl cellulose or modified cellulose such as microcrystalline cellulose, hydroxypropyl cellulose, sugars such as sucrose and lactose, or sugar alcohols such as xylitol, sorbitol or maltitol, polyvinylpyrrolidone and polyethylene glycol), wetting agents, antibacterials, chelating agents, coatings (such as a cellulose film coating, synthetic polymers, shellac, corn protein zein or other polysaccharides, and gelatin), preservatives (including vitamin A, vitamin E, vitamin C, retinyl palmitate, and selenium, cysteine, methionine, citric acid and sodium citrate, and synthetic preservatives, including methyl paraben and propyl paraben), sweeteners, perfuming agents, flavoring agents, coloring agents, administration aids, and combinations thereof.

Carriers are compounds and substances that improve and/or prolong the delivery of a TFD-containing glycopeptide to a subject in the context of an edible formulation or a pharmaceutical formulation. Carrier may serve to prolong the in vivo activity of a TFD-containing glycopeptide or slow the release of the TFD-containing glycopeptide in a subject, using controlled-release technologies. Carriers may also decrease TFD-containing glycopeptide metabolism in a subject and/or reduce the toxicity of TFD-containing glycopeptides. Carrier can also be used to target the delivery of the TFD-containing glycopeptide to particular cells or tissues in a subject. Common carriers (both hydrophilic and hydrophobic carriers) include fat emulsions, lipids, PEGylated phospholids, PEGylated liposomes, PEGylated liposomes coated via a PEG spacer with a cyclic RGD peptide $c(RGD^PYK)$, liposomes and lipospheres, microspheres (including those made of biodegradable polymers or albumin), polymer matrices, biocompatible polymers, protein-DNA complexes, protein conjugates, erythrocytes, vesicles, nanoparticles, and side-chains for hydro-carbon stapling. Carriers may also be used in formulations for other uses, such as research uses in vitro (e.g., for delivery to cultured cells) and/or in vivo.

Edible formulations for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils, e.g. vegetable oils, may be used to provide oil-in-water or water in oil suspensions. In certain situations, delayed release preparations may be advantageous and compositions which can deliver the TFD-containing glycopeptide in a delayed or controlled release manner may also be prepared. Prolonged gastric residence brings with it the problem of degradation by the enzymes present in the stomach and so enteric-coated capsules may also be prepared by standard techniques in the art where the active substance for release lower down in the gastro-intestinal tract.

Pharmaceutical formulations adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water-for-injection, alcohols, polyols, glycerine and vegetable oils, for example. The formulations may be presented in unit-dose or multi-dose containers, for example sealed ampoules and vials, and may be stored in a freeze-dried (lyophilized) condition requiring only the addition of the sterile liquid carrier, for example water or saline for injections, immediately prior to use. Extemporaneous injection solutions and suspensions may be prepared from sterile powders, granules and tablets. The pharmaceutical formulations may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically-active agents in addition to the TFD-containing glycopeptides of the present invention.

Administration frequencies for TFD-containing glycopeptide formulations of the present invention (i.e., doses) include 4, 3, 2 or once daily, every other day, every third day, every fourth day, every fifth day, every sixth day, once weekly, every eight days, every nine days, every ten days, bi-weekly, monthly and bi-monthly. The duration of administration will be based on the condition being treated, prevented or reduced, and will be best determined by the attending physician. However, continuation of administration is contemplated to last for a number of days, weeks, months or years. In some instances, administration may continue for the entire life of the subject.

Depending on the means of administration, each dose of the formulations may be administered all at once, such as with an oral formulation in a capsule or liquid, or slowly over a period of time, such as with parenteral administration, e.g., i.p. administration.

The amount of TFD-containing glycopeptide in each dose administered to a subject will vary depending on the physical characteristics of the formulation (e.g., edible formulation versus an i.p. formulation), the means used to administer the formulation and the purpose underlying the administration. However, when administered in an edible formulation, each dose will contain from about 1 mg/kg to about 500 mg/kg of the TFD-containing glycopeptide to the body weight of the subject. When administered in an i.p. formulation, each dose will contain from about 1 mg/kg to about 100 mg/kg of the TFD-containing glycopeptide to the body weight of the subject, including from about 1 mg/kg to about 100 mg/kg, from about 5 mg/kg to about 50 mg/kg, from about 10 mg/kg to about 30 mg/kg, and about 10 mg/kg, 11 mg/kg, 12 mg/kg, 13 mg/kg, 14 mg/kg, 15 mg/kg, 16 mg/kg, 17 mg/kg, 17.5 mg/kg, 18 mg/kg, 19 mg/kg, 20 mg/kg, 21 mg/kg, 22 mg/kg, 23 mg/kg, 24 mg/kg, and 25 mg/kg.

In each of the methods of the present invention that are related to cancer, the term "cancer" is intended to be broadly interpreted and it encompasses all aspects of abnormal cell growth and/or cell division, limited only in that cancer cells express a galectin, such as gal3, gal4 or gal9N, or an TF-antigen, such as TFD. Examples include, but are not limited to, carcinoma, including but not limited to adenocarcinoma, squamous cell carcinoma, adenosquamous carcinoma, anaplastic carcinoma, large cell carcinoma, small cell carcinoma, and cancer of the skin, breast, prostate, bladder, vagina, cervix, uterus, liver, kidney, pancreas, spleen, lung, trachea, bronchi, colon, small intestine, stomach, esophagus, gall bladder; sarcoma, including but not limited to chondrosarcoma, Ewing's sarcoma, malignant hemangioendothelioma, malignant schwannoma, osteosarcoma, soft tissue sarcoma, and cancers of bone, cartilage, fat, muscle, vascular, and hematopoietic tissues; lymphoma and leukemia, including but not limited to mature B cell neoplasms, such as chronic lymphocytic leukemia/small lymphocytic lymphoma, B-cell prolymphocytic leukemia, lymphomas, and plasma cell neoplasms, mature T cell and natural killer (NK) cell neoplasms, such as T cell prolymphocytic leukemia, T cell large granular lymphocytic leukemia, aggressive NK cell leukemia, and adult T cell leukemia/lymphoma, Hodgkin lymphomas, and immunodeficiency-associated lymphoproliferative disorders; germ cell tumors, including but not limited to testicular and ovarian cancer; blastoma, including but not limited to hepatoblastoma, medulloblastoma, nephroblastoma, neuroblastoma, pancreatoblastoma, leuropulmonary blastoma and retinoblastoma. The term also encompasses benign tumors. In one aspect, the cancer is prostate cancer.

In each of the methods of the present invention that are directed to methods performed in a subject, the subject is a human, a non-human primate, bird, horse, cow, goat, sheep, a companion animal, such as a dog, cat or rodent, or other mammal. Furthermore, the subject may be a subject having cancer or a subject at risk for developing cancer. The cancer may be benign, pre-metastatic or metastatic.

As used herein, the terms "reduce" and "reducing", "suppress" and "suppressing", and "inhibit" and "inhibiting" through the use of TFD-containing glycopeptides, such as $TFD_{100}$, have their ordinary and customary meanings and include one or more of: reducing, suppressing, or inhibiting an action or an activity. Preferably, the reducing is about 100%, 99%, 98%, 97%, 96%, 95%, 90%, 80%, 70%, 60%, 50%, 40%, 30%, 20%, 10%, 5% or 1% versus circumstances in which a TFD-containing glycopeptide, such as $TFD_{100}$, is not used. For example, as used herein "reducing gal3 activity" using a TFD-containing glycopeptide, such as $TFD_{100}$, is an reduction in gal3 activity of about 100%, 99%, 98%, 97%, 96%, 95%, 90%, 80%, 70%, 60%, 50%, 40%, 30%, 20%, 10%, 5% or 1% versus circumstances in which the TFD-containing glycopeptide, such as $TFD_{100}$, is not used.

Preferably, the suppressing is about 100%, 99%, 98%, 97%, 96%, 95%, 90%, 80%, 70%, 60%, 50%, 40%, 30%, 20%, 10%, 5% or 1% versus circumstances in which a TFD-containing glycopeptide, such as $TFD_{100}$, is not used. For example, as used herein "suppressing metastasis" using a TFD-containing glycopeptide, such as $TFD_{100}$, is a suppression of metastasis of about 100%, 99%, 98%, 97%, 96%, 95%, 90%, 80%, 70%, 60%, 50%, 40%, 30%, 20%, 10%, 5% or 1% versus circumstances in which the TFD-containing glycopeptide, such as $TFD_{100}$, is not used.

Preferably, the inhibiting is about 100%, 99%, 98%, 97%, 96%, 95%, 90%, 80%, 70%, 60%, 50%, 40%, 30%, 20%, 10%, 5% or 1% versus circumstances in which a TFD-containing glycopeptide, such as $TFD_{100}$, is not used. For example, as used herein "inhibiting gal3-TFD binding" using a TFD-containing glycopeptide, such as $TFD_{100}$, is an inhibition in binding of about 100%, 99%, 98%, 97%, 96%, 95%, 90%, 80%, 70%, 60%, 50%, 40%, 30%, 20%, 10%, 5% or 1% versus circumstances in which the TFD-containing glycopeptide, such as $TFD_{100}$, is not used.

As used herein, the terms "protect" and "protecting" through the use of TFD-containing glycopeptides, such as $TFD_{100}$, have their ordinary and customary meanings and include keeping or maintaining an action or activity. Preferably, the protecting is about 100%, 99%, 98%, 97%, 96%, 95%, 90%, 80%, 70%, 60%, 50%, 40%, 30%, 20%, 10%, 5% or 1% versus circumstances in which a TFD-containing glycopeptide, such as $TFD_{100}$, is not used. For example, as used herein "protecting $CD8^+$ activity" using a TFD-containing glycopeptide, such as $TFD_{100}$, is a protection of $CD8^+$ activity of about 100%, 99%, 98%, 97%, 96%, 95%, 90%, 80%, 70%, 60%, 50%, 40%, 30%, 20%, 10%, 5% or 1% versus circumstances in which the TFD-containing glycopeptide, such as $TFD_{100}$, is not used.

The invention also provides a kit comprising one or more containers filled with TFD-containing glycopeptides, such as $TFD_{100}$. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

IV. Examples

Materials and Methods

Cell Culture.

Androgen-independent prostate cancer cell line PC3 (ATCC, Manassas, Va.) and PC-3-Luc (kind gift from Dr. Patrick J. Casey, Duke University, Durham, N.C.) were cultured in a mixture of DMEM (Sigma, St. Louis, Mo.) and F-12 (Sigma) (1:1) supplemented with 10% fetal bovine serum (FBS) (Quality Biologicals, Gaithersburg, Md.), 100 units/ml penicillin G sodium and 100 μg/ml streptomycin sulfate (Sigma). Human umbilical vein endothelial cells (HUVEC) (Lonza, Switzerland) were maintained in EGM2 basal medium supplemented with Bullet kit (Lonza). The human T cell line MOLT-4 (ATCC), Jurkat (gift of Dr. Agnes Azimzadeh, University of Maryland, Baltimore), $CD8^+$ T-cells isolated from peripheral blood mononuclear cells (PBMCs), and pmel T cells were grown in RPMI 1640 containing 2 mM glutamine, penicillin-streptomycin, and 10% FBS. All cells were cultured in the presence of 5% $CO_2$ at 37° C.

Purification of TFD-Containing Compounds from Cod Fish.

TFD-containing compounds were purified either from extraction of Pacific cod purchased from local store or from cod-derived anti-freeze glycoproteins purchased from A/F Protein (Waltham, Mass.). Extraction of cod (900 gm) was performed in 1 liter of Tris-buffered saline (TBS, 50 mM Tris, 100 mM NaCl, 1 mM $CaCl_2$, 1 mM $MgCl_2$, 1 mM $MnCl_2$, pH 8.0) containing 100 μM PMSF and after centrifuging at 8000×g for 30 min at 4° C., the clear supernatant was passed through a column of peanut agglutinin-agarose (Sigma) (that was pre-equilibrated with the TBS). The column was washed with TBS until no protein was detected in the washing (monitored at 214 nm) and the bound protein was eluted with 100 mM lactose in the TBS. The lactose eluate was dialyzed with water and further fractionated by fast performance liquid chromatography (Amersham) on a size exclusion column Superdex 75. Inhibitory activity of each peak was investigated on galectin-3 binding to asialofetuin on a 96-well plate (see later). The purified TFD-containing glycoprotein corresponding to ~100 kDa (designated as $TFD_{100}$) was used in angiogenesis, tumor-endothelial cell interaction, and apoptosis experiments.

Preliminary investigation on the nature of the carbohydrates and their activities to inhibit gal3 binding was performed after size fractionation of crude anti-freeze glycoproteins (purchased from A/F Protein, Waltham, Mass.) using Centricon membrane devices of various molecular weight cut-off such as 50 kDa, 30 kDa, 10 kDa, and 3 kDa (2 ml capacity) (Millipore, MA). Briefly, 50 mg of crude glycoproteins in 2 ml of water was taken in a Centricon device of 50 kDa cut-off and centrifuged at 5000×g to approximately 100 μl (approximately 1 hour) at 4° C. using J20 rotor (Beckman centrifuge). The retentate on the centricon membrane was diluted to 2 ml with water and re-centrifuged. This process of dilution and centrifugation was continued two more of times. At the end of this process, the retentate (designated as Fraction 1) was collected and saved for further characterization. The filtrate was processed for further fractionation on 30 kDa MW cut-off centricon device and so on as described above. Thus, the partial purification resulted in five fractions (Fr) as follows: Fr1 (>50 kDa); Fr2 (<50 kDa, but >30 kDa); Fr3 (<30 kDa, but >10 kDa); Fr4 (<10 kDa, but >3 kDa); and Fr5 (<3 kDa). Each fraction was freeze-dried and stored at −20° C. until further characterization. The Fr1 was further purified on a peanut agglutinin (PNA)-agarose column (Sigma) as described above.

Biacore Kinetics and Affinity Analysis.

The binding kinetics and affinity of a few carbohydrates for gal3 were measured in Surface Plasmon Resonance (SPR)-based binding assays using a Biacore™ T200 instrument (GE Healthcare). Biotinylated gal3 was attached to Biacore Sensor Chip SA (GE Healthcare) according to the instructions. For this purpose, biotinlyated gal3 was diluted into HBS-EP+ (GE Heathcare) to a concentration of 1 μg/mL and captured onto the streptavidin surface to a final level of 1750 RU. A reference surface was prepared with biotin captured onto the streptavidin. Binding kinetics and affinity of carbohydrate ligands (such as lactose, N-acetyllactosamine, TFD, and TFD100) were measured using a titration of concentrations in 2-fold dilutions that spanned the $K_d$. The binding response of small carbohydrate ligands were measured in Resonance units (RU) in real time at 10 HZ. These carbohydrates were injected for 30 seconds at 50 μL/min, and 30 seconds of dissociation data were collected. For $TFD_{100}$ binding assay, lower density surface of 550 RU of biotinlyated gal3 was prepared. The binding of $TFD_{100}$ exhibited significantly slower kinetics and required injections for 120 seconds, and collection of 600 seconds of dissociation data. The slow dissociation of $TFD_{100}$ prompted regeneration of the gal3 surface using a 60 second injection of 100 mM lactose. Raw sensorgram data were reference subtracted and blank subtracted prior to kinetic and affinity analysis. Biacore™ T200 Evaluation software was used for Steady-state affinity analysis and kinetic analysis. The association and dissociation rates for lactose binding approached the resolution limit of the instrument, therefore a plot of response at equilibrium versus concentration was used for steady-state analysis of the KD. The association and dissociation rates, as well as the KD for $TFD_{100}$ binding were determined using a simple 1:1 binding model.

Histochemical Analyses of Normal and Tumor Prostate Tissues.

Immunohistochemical detection of gal3 using specific anti-gal3 antibody was performed on 5 μm thick paraffin-embedded sections containing the most representative tumor areas. In brief, sections were deparaffinized in xylene, hydrated through graded concentrations of ethanol and then with distilled water. Samples were heated in a microwave oven in 1× Target Retrieval solution and then washed with PBS for 5 min. All sections were incubated in 3% hydrogen peroxide to inhibit endogenous peroxidase. Protein A-Sepharose purified anti-gal3 antibody (10 µg/ml) (34) was applied to the slides and incubated for 30 min at room temperature in a humidified chamber. Protein A-Sepharose purified pre-immune rabbit serum was used as control. Sections were incubated with post primary block for 15 minutes and polymer for 15 minutes (NovoLink Polymer kit, Novocastra, Vision BioSystems, Newcastle-upon-Tyne, UK). Staining was visualized with the diaminobenzidine (DAB) chromogen and counterstained with Mayer's hematoxylin.

To investigate TFD expression, prostate tissue (normal and tumor) array (US Biomax, Inc., Rockville, Md.) was subjected to binding with peanut lectin-FITC (EY Laboratories, Inc.) and after washing the binding was visualized under fluorescence microscope.

Analytical Procedures.

Crude, membrane-fractionated, and purified TFD containing glycoproteins were investigated for the presence of TFD using glycan differentiation kit (Roche, Indianapolis, Ind.) following the manufacturer's instructions. The carbohydrate content (neutral hexose) was measured by phenol-sulfuric acid assay (35). Analytical PAGE in the presence of SDS (2%) was carried out on a NuPAGE Novex 4-12% Bis-Tris gels (Invitrogen) under reducing or non-reducing conditions as reported elsewhere (36). The protein content was measured at 214 nm using bovine serum albumin (BSA) as a standard. In some cases, protein concentration was measured with Coomassie Blue dye as previously described (37).

Solid Phase Binding-Inhibition Assay.

The inhibitory activity of $TFD_{100}$, other TFD-containing fractions, and O-glycosidase treated $TFD_{100}$ on gal3 binding was determined using a solid phase assay as previously described (37). Briefly, asialofetuin (0.5 µg/100 µl/well) in 0.1 M $Na_2CO_3$/0.02% $NaN_3$ (pH 9.6) was adsorbed onto the wells of microtiter plates (Immulon; Dynatech Laboratories, Chantilly, Va.) at 37° C. for 3 h, and the bound glycoprotein was fixed with 2% formaldehyde in phosphate-buffered saline (PBS, 10 mM phosphate, 140 mM NaCl, pH 7.5) at 37° C. for 30 min. The plates were washed three times with PBS (azide-free)/0.05% Tween 20, and incubated with the gal3-biotin conjugate (10 ng/100 µl/well for binding assays) or with preincubated mixture of equal volume of conjugate and varying concentrations of test ligands (for binding-inhibition assays). After incubation for 1 h at 4° C., the plates were washed with ice-cold azide-free PBS-Tween 20, and the bound conjugate was allowed to interact with peroxidase labeled streptavidin (0.05 µg/100 µl well) in azide-free PBS-Tween for 1 h at 4° C. The plate was washed with ice-cold azide free PBS-Tween and the bound peroxidase activity was assayed with peroxidase substrate diammonium 2,2'-azinobis (3-ethylbenzothiazoline-6-sulfonate) (KPL, Rockville, Md.) (37). To prepare gal3-biotin conjugate, 0.5 mg of the purified recombinant gal3 as previously described (34) in 0.5 ml of azide free PBS/0.1 M lactose was mixed with 0.5 mg of EZ-Link™ Sulfo-NHS-LC-Biotin (Thermo Scientific, Rockford, Ill.) in 50 µl PBS. After incubation for 2 h on ice, the mix was dialyzed with PBS and purified by affinity chromatography on lactosyl-Sepharose (37). The purified gal3-biotin conjugate was dialyzed with PBS and stored in 1% BSA-50% glycerol at −20° C. until further use. For O-glycosidase treatment, 10 µg of $TFD_{100}$ was incubated with 1 µl of O-glycosidase (Roche) at 37° C. for about 16 h. The treated $TFD_{100}$ was then desalted on a PD10 column (Bio-Rad) and used on the solid phase assay. O-Glycosidase treatment removes TF-disaccharide from protein (cleaves GalNAc-Ser/Thr linkage).

Binding of $TFD_{100}$ with Other Galectins.

The inhibitory activity of $TFD_{100}$ on binding of other galectins such as gal4, and N-terminal of gal9 (gal9N) was determined on solid phase assay as described above. Briefly, galectin (for binding) or mixture of fixed amount of galectin and varying amount of $TFD_{100}$ (for binding inhibition) was added to asialofetuin adsorbed wells and after washing the bound galectin was mixed with the anti-galectin antibody followed by the addition of secondary antibody conjugated HRP and development with ABTS substrate as above.

Angiogenesis.

Induction of angiogenesis in the presence of gal3 and the inhibition of angiogenesis in the presence of $TFD_{100}$ or lactose were performed using Chemicon's In vitro angiogenesis kit (Millipore, MA) following the manufacturer's instructions. Briefly, $5\times10^4$ HUVEC cells were seeded in matrigel coated 96 well plate in the presence or absence of gal3, $TFD_{100}$, or lactose alone or in combination with gal3+$TFD_{100}$ or gal3+lactose. After 5 h, the microvessel formation was analyzed under phase contrast microscope at the 10× magnification. For quantitation of tube formation, the number of branching was counted in six areas (each 25 $nm^2$) of each well and an average value was taken.

Extracellular Localization of Gal3 and TFD in PC3 and HUVEC.

The extracellular localization of gal3 in the PC-3 cells was investigated with anti-gal3 antibody on a flow cytometer (Becton Dickinson FACSCanto II). Briefly, confluent cells were washed with PBS-5 mM EDTA, separated from the plate, and incubated with 10 µg/ml of protein A-Sepharose purified polyclonal rabbit anti-gal3 antibody (34) for 30 min at 4° C. After washing with PBS for 3 times using centrifugation (200×g) for 5 min each, the cells were incubated with 0.8 µg/ml DyLight 649 labeled goat anti-rabbit IgG (KPL). The washed cells were then subjected to the flow cytometry and acquired at FL4 channel. The extracellular localization of TFD in the PC3 and HUVEC cells was investigated with PNA-FITC (EY Laboratories) and subjected to the flow cytometry. The cells were analyzed through FL1 channel. The presence of TFD-containing glycoprotein in PC3 and HUVEC cells was also investigated by using glycan differentiation kit (Roche) as described above.

Tumor-Endothelial Cell Interactions.

For adhesion to endothelial cells, HUVEC was grown to confluence and single-cell suspension of calcein labeled (eBioscience, San Diego, Calif.) PC-3 cells were allowed to bind to HUVEC in the presence of $TFD_{100}$, gal3 siRNA, lactose, and various antibodies as previously described (38). Inhibition of tumor-endothelial cells was performed in three different ways. 1. The calcein labeled PC-3 cells were treated with various reagents and after washing, the cells were allowed to bind to HUVEC. 2. HUVEC cells were treated with various reagents and the labeled PC3 cells were allowed to bind to the washed HUVEC. 3. The interaction of labeled PC3 to HUVEC was performed in the presence of $TFD_{100}$ and gal3 siRNA. The binding or binding-inhibition in each well was examined by phase contrast microscopy at 10× magnification and quantitated on a spectrofluorimeter (SpectraMax M5 Multimode Microplate Reader from Molecular Devices, CA) using calcein AM Ex/Em—495/515.

Apoptosis of T Cells (MOLT-4, Jurkat, and $CD8^+$ Cells).

Gal3-mediated apoptosis of MOLT-4 cells in the presence or absence of $TFD_{100}$ was assessed by measuring apoptotic cells by annexin V binding (Oncogene, Inc) on a flow cytometer. Jurkat cells were used for gal3-mediated apoptosis at various concentration of gal3. To investigate gal3-mediated apoptosis of human CD8+ cells, peripheral blood mononuclear cells (PBMCs) were isolated from chronic leukemia patients using Ficoll-paque density gradient method (39) followed by negative selection of CD8+ cells with a cocktail of antibodies using a kit (BD Biosciences, MD). The presence of CD8+ cells in the purified fraction was confirmed by staining cells with anti-CD8 antibody. For apoptosis, CD8+ T cells were treated with gal3 (5 μM) in the presence or absence of $TFD_{100}$ (3.5 nM) or lactose (50 μM) and apoptotic cells were measured by annexin V binding.

To investigate if tumor-associated gal3 can induce tumor specific CD8 T cells, we used B16 melanoma-specific transgenic D90.1 CD8 T cells (pmel T cells) (40). After harvesting T cells from mouse spleen, cells were activated with a peptide (40), mixed with a monolayer of B16 melanoma cells and apoptosis was measured by Annexin V binding after gating with anti-CD8 antibodies. To investigate if patient serum associated gal3 can induce apoptosis of CD8 cells, prostate cancer patient serum (intact or gal3-depleted) was mixed with activated pmel T cells and apoptosis was measured in the presence or absence of $TFD_{100}$ (3.5 nM).

Experimental Metastasis Assay.

Confluent culture of PC3-Luc cells was scraped and resuspended at $1 \times 10^6$ cells/ml in PBS. $1 \times 10^5$ cells were then injected intravenously into the tail vein of 8 Nude mice (3-4 weeks old, Strain Ncrnu-F, vendor: Taconic) restrained by mouse tail illuminator tail vein injection apparatus (Braintree Scientific). Mice were separated into two groups. One group received $TFD_{100}$ (50 μl of 7 μg/ml per mouse, 17.5 μg per kg body weight) intraperitoneally twice a week for a period of 9 weeks; while the other group received only PBS. Prior to imaging, mice were injected intraperitoneally with Luciferin (150 mg/kg, Xenogen) and returned to their cages for 5 min to allow for biodistribution. Mice were anesthetized with 2% isoflurane gas (integrated within the Xenogn IVIS-200 system) and imaged 5 mins for a single-photon emission. Total photon flux (photons/sec) was calculated and corrected for tissue depth by spectral imaging using Living Image 3.0 software (Xenogen).

Statistical Analysis.

The statistical analyses were performed using one-way analysis of variance (ANOVA) followed by Turkey-Kramer multiple comparisons (Graphpad Instat, version 3). The differences were considered significant when $p<0.05$.

Results

Purification and Characterization of $TFD_{100}$.

Figure 7:
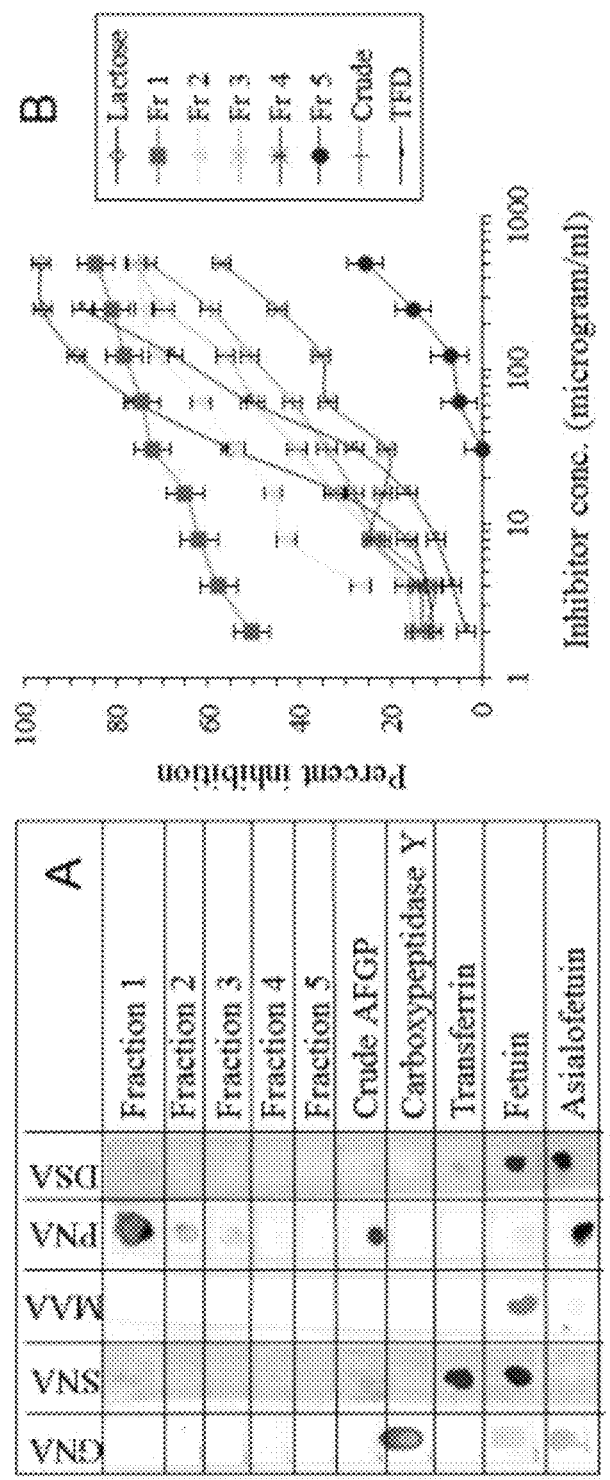
FIG. 7. Characterization of various TFD-containing compounds.

A preliminary analysis of size-based fractionation of commercial cod fish glycoproteins (AFGP, A/F Proteins) using Centricon tubes resulted five fractions, of which only three fractions (Fr 1-3) had TFD (Galβ1,3GalNAc) as confirmed by positive reaction with the peanut lectin (PNA) using Glycan Differentiation Kit (Table 1; FIG. 7A). The inhibitory activity of various fractions on gal3 binding was determined using a solid phase assay and Fr1 was found very active (FIG. 1B). Based on these results, the follow up purification procedure was aimed to select the most active fraction. For this purpose, either commercial AFGP (cod glycoproteins) or crude extract of whole cod was subjected to affinity purification followed by gel permeation chromatography. Gel permeation chromatography of the affinity purified TFD-containing glycopeptides yielded two major peaks corresponding to ~100 kDa (designated as $TFD_{100}$) and 4 kDa, respectively (FIG. 1A). The 100 kDa peak ($TFD_{100}$) exerted many fold higher inhibitory effect than the 4 kDa peak on gal3 binding (FIG. 1C). On SDS-PAGE under reducing condition $TFD_{100}$ migrated as a diffused band with an apparent $M_r$ of ~100 kDa (FIG. 1B, ii). The presence of TFD in that peak was further established with a Western blot analysis followed by PNA binding (FIG. 1B, iii). Considering the molar concentration, $TFD_{100}$ ($I_{50}$ at 0.25 nM) was 800,000-fold active in inhibiting gal3 binding compared to free TFD ($I_{50}$ at 200 μM); while the 4 kDa peak was inactive even at 37 nM (FIG. 1C). The importance of O-glycan in gal3-$TFD_{100}$ interaction was confirmed with an O-glycosidase treated $TFD_{100}$, which was significantly less inhibitory (45% inhibition at 6.2 nM, FIG. 1C).

TABLE 1

Characterization of various fractions from centricon centrifugation

| Sample | Molecular size | % Yield | % Protein | % Hexose (Neutral) | Type of glycan | $I_{50}$ value (μg/ml) | RIA |
|---|---|---|---|---|---|---|---|
| Lactose | 360 Da | NA | NA | NA | NA | 27 | 1 |
| TFD | 383 Da | NA | NA | NA | NA | 58 | 0.47 |
| Crude extract | | NA | 1.1 | 46 | Galβ1,3GalNAc— | 108 | 0.25 |
| Fraction 1 | >50 kDa | 3.3 | 2.6 | 23 | Galβ1,3GalNAc— | 2.5 | 10.5 |
| Fraction 2 | <50 kDa, >30 kDa | 1.9 | 0.7 | 20 | Galβ1,3GalNAc— | 27 | 1 |
| Fraction 3 | <30 kDa, >10 kDa | 18.4 | 1.0 | 39 | Galβ1,3GalNAc— | 82 | 0.33 |
| Fraction 4 | <10 kDa, >3 kDa | 35.0 | 0.6 | 48 | ND | 300 | 0.09 |
| Fraction 5 | <3 kDa | 41.3 | 0.5 | 9 | ND | >500 | <0.06 |

% Yield, by dry weight; % Protein, by Coomassie staining (37); RIA, Relative inhibitory activity compared to lactose (taken as 1); NA, Not applicable; ND, No glycan detected with Glycan Differentiation Kit.

Figure 8:
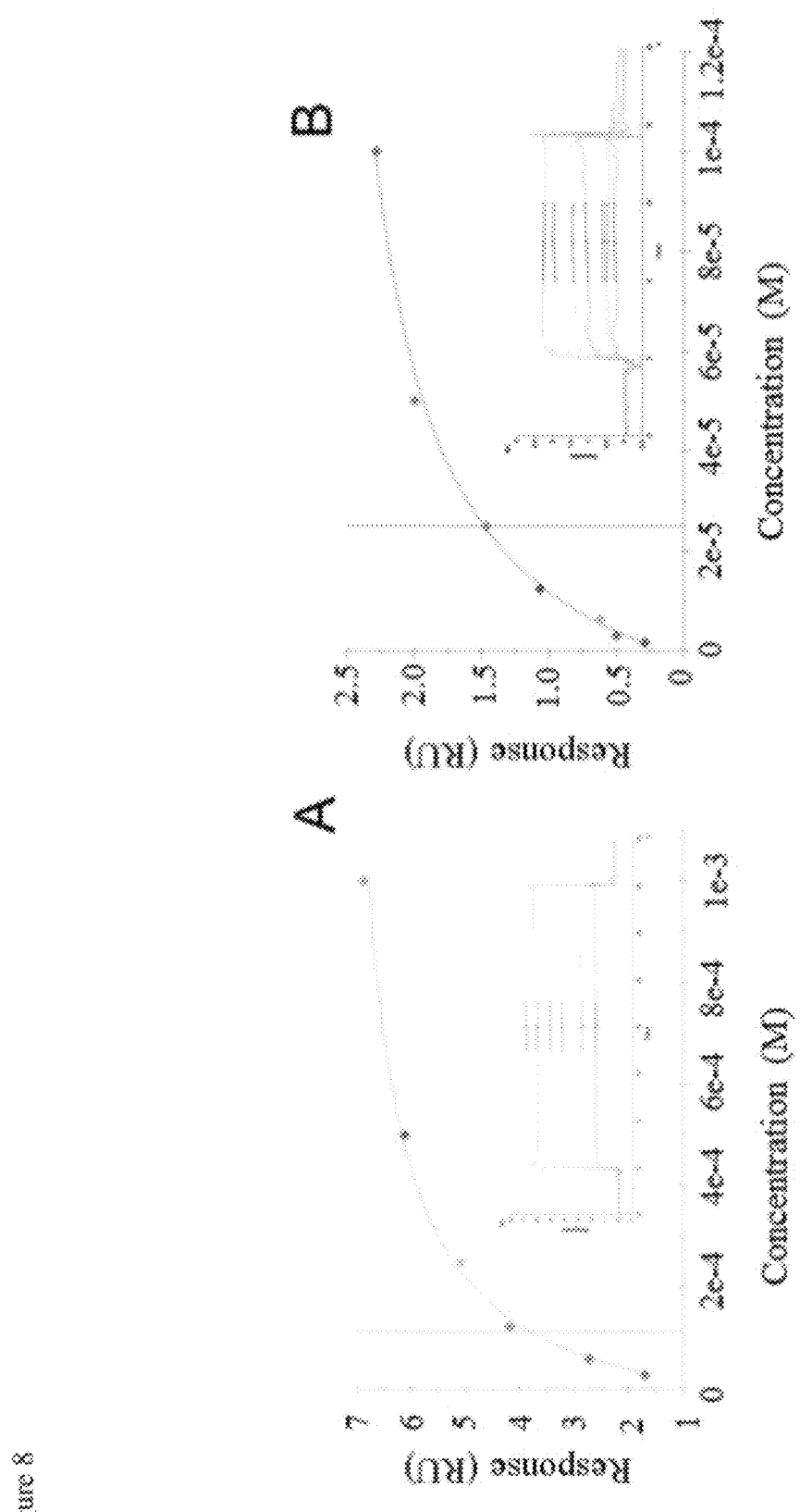
FIG. 8. Surface plasmon resonance assay on Biacore. Binding kinetics and affinity of lactose (FIG. 8A) and N-acetyllactosamine (FIG. 8B) for gal3 were measured were measured using a titration of concentrations in 2-fold dilutions that spanned the KD. Lactose was measured from 31 μM to 1000 μM, and the KD was determined to be $1.1^{e-4}$ (M) or 110 μM. N-Acetyllactosamine was measured from 1.56 μM to 100 μM, and the KD was determined to be $2.5^{e-5}$ (M) or 25 μM.

The binding kinetics and affinity of $TFD_{100}$ to gal3 was characterized in an SPR-based assay. The $TFD_{100}$ binding interaction with gal3 was compared with the gal3 binding to lactose, N-acetyllactosamine, and TFD (Galβ1,3GalNAc) to assess whether differences in the speed and strength of binding could be shown. Lactose ($K_d$ 110 μM) (FIG. 8A), N-acetyllactosamine ($K_d$ 25 μM) (FIG. 8B), and TFD ($K_d$ 636 μM) exhibited extremely fast association and dissociation rates that were beyond the limits of resolution for reliable kinetic analysis (FIG. 1D). Steady-state affinity analysis provided a means of comparing the equilibrium dissociation constants to that of $TFD_{100}$ binding (FIG. 1E). These Biacore assays revealed that $TFD_{100}$ bound to gal3 with significantly higher affinity compared to all other carbohydrates measured. The interaction of $TFD_{100}$ with gal3 exhibited an affinity that was stronger than the other carbohydrates by approximately 6 orders of magnitude ($K_d$ 97 pM). This difference in affinity was primarily driven by a considerably slower dissociation rate for $TFD_{100}$, which is indicative of a very stable complex. The measured dissociation rate of $3^{e-4}$ per second is equivalent to a half-life for the complex of 38.5 minutes. This is in contrast to the interactions with the other carbohydrates which had half-lives that were less than 1 second.

The relative binding activity of $TFD_{100}$ towards gal4 and gal9N was also investigated on solid phase assay. Like gal3 ($I_{50}$ 0.25 nM), the interaction of asialofetuin with either gal4 ($I_{50}$ 1.2 nM) and gal9N ($I_{50}$ 1.5 nM) was inhibited by the $TFD_{100}$. However, with respect to lactose $TFD_{100}$ was approximately $4 \times 10^5$ fold better in the case of gal3, $8.3 \times 10^6$ for gal4, and $6.7 \times 10^4$ for gal9N (Table 2).

TABLE 2

Inhibition of galectin binding to asialofetuin by lactose and $TFD_{100}$

| Galectin | Lac $I_{50}$ value (μM) | $TFD_{100}$ $I_{50}$ value (nM) | RIA |
|---|---|---|---|
| Gal3 | 100 | 0.25 | 400,000 |
| Gal4 | 10,000 | 1.2 | 8,333,333 |
| Gal9N | 100 | 1.5 | 66,667 |

RIA, Relative inhibitory activity compared to lactose taken as 1

$TFD_{100}$ Inhibits Angiogenesis.

Figure 2:
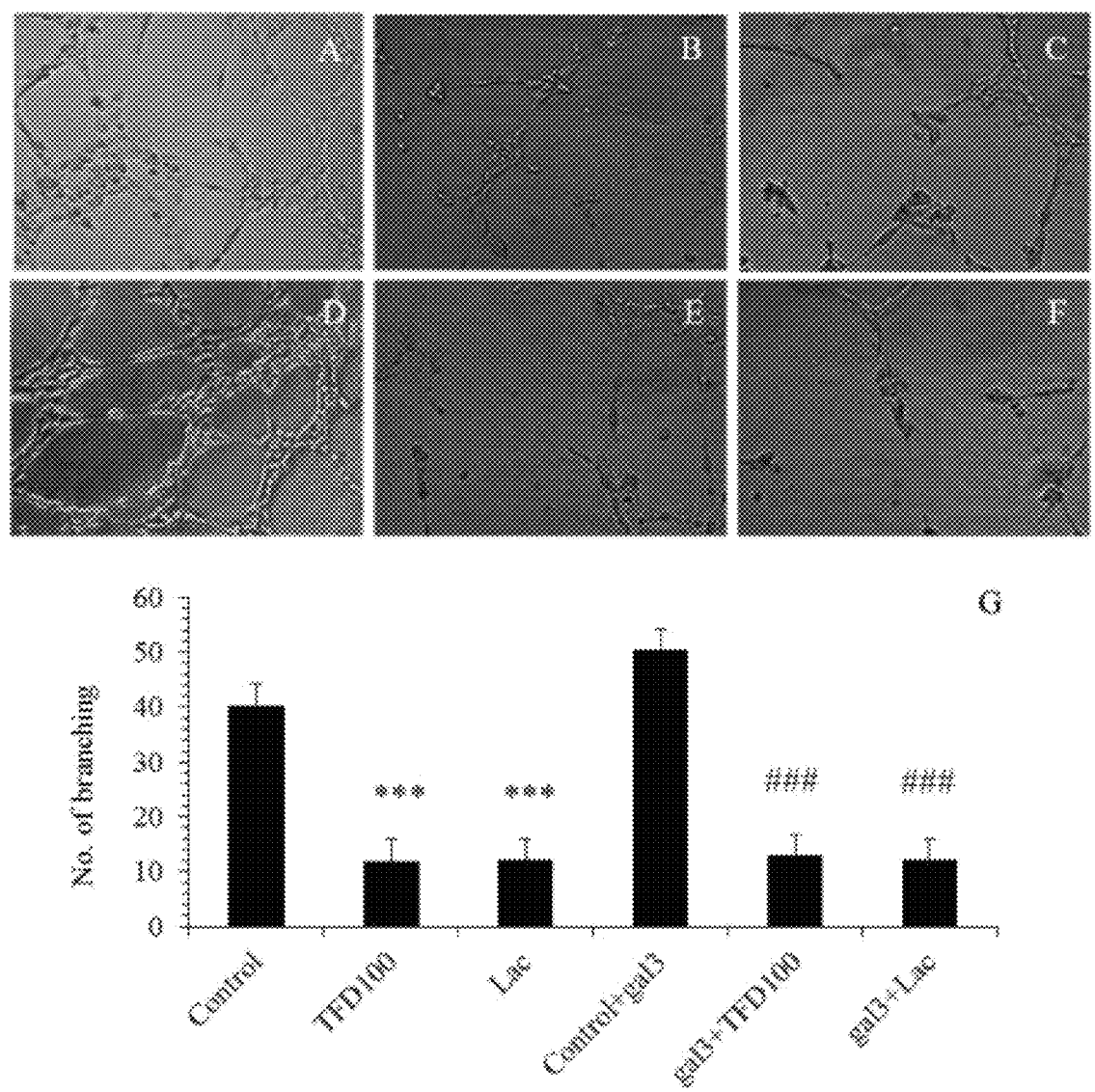
FIG. 2. Angiogenesis of HUVEC in absence (FIGS. 2A-C) or presence (FIGS. 2D-F) of external gal3 and inhibition of angiogenesis with 3.5 nM TFD$_{100}$ (FIGS. 2B, E) or 50 μM lactose (FIGS. 2D, F) as examined on a phase contrast microscopy.

As angiogenesis is an essential step of metastasis, $TFD_{100}$ was investigated for its inhibitory activity on angiogenesis. HUVEC cells rapidly align and form hollow tube-like structures when grown in certain media (FIG. 2A). Interestingly, tube formation was enhanced by ~25% in presence of recombinant gal3 (5 μM) (FIG. 2D) as quantitated by counting the number of branching. The tube formation was inhibited by 70-75% with 3.5 nM $TFD_{100}$ (FIGS. 2B, E, G) suggesting the role of lectin-carbohydrate interaction in angiogenesis.

$TFD_{100}$ Inhibits Tumor-Endothelial Cell Interactions.

Figure 3:
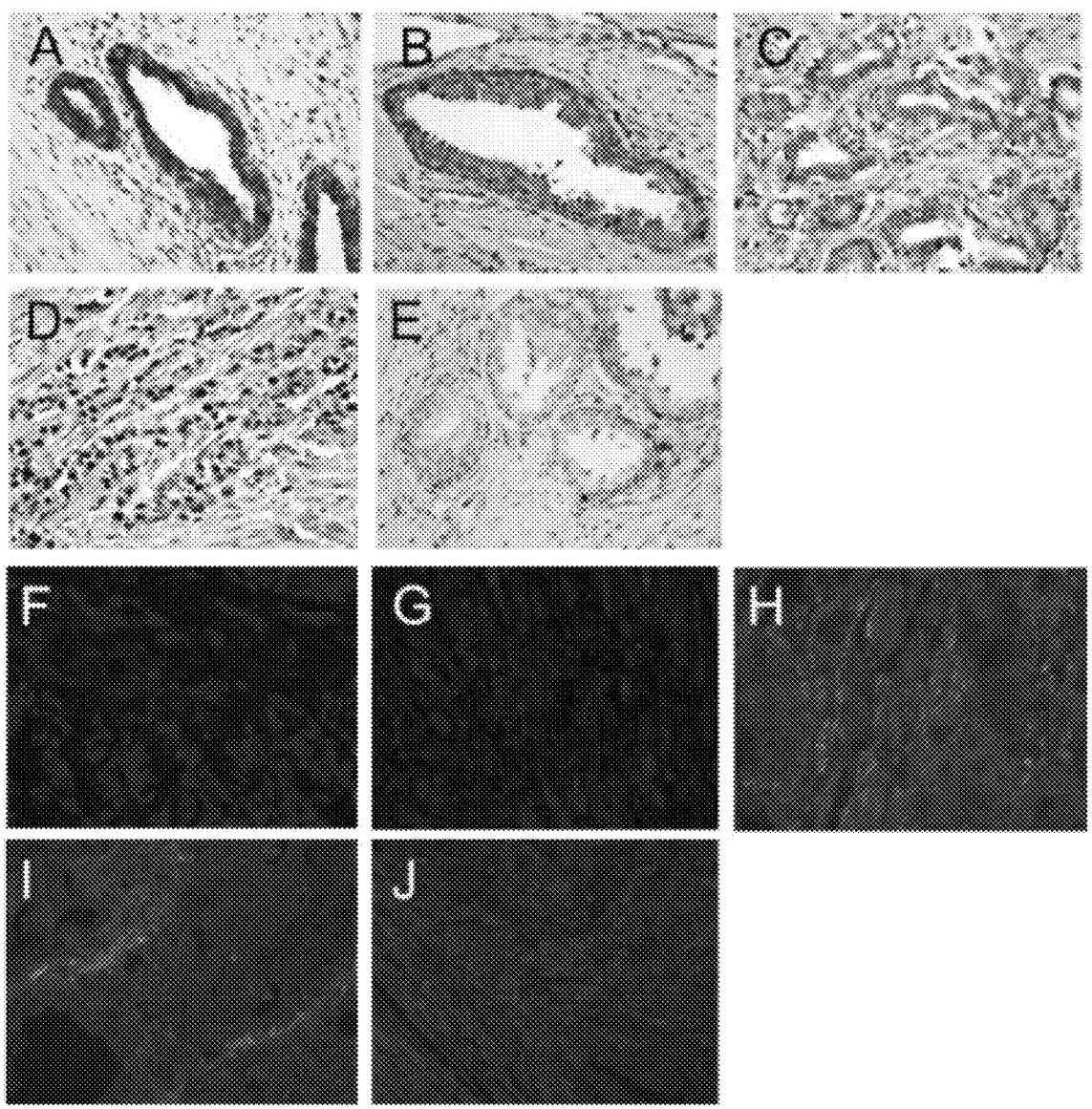
FIG. 3. Expression of gal3 and TFD in prostate tissues as determined by immunostaining with affinity purified specific anti-gal3 antibodies. Representative results; magnification, ×400.

To examine the relevance of in vitro data to in vivo, expression of gal3 first investigated (this study and also ref. 21) and TFD in normal, BPH, and various stages of PCa (FIG. 3). Gal3 was found to be strongly expressed in benign prostatic hyperplasia (BPH) (FIG. 3A). However, expression of gal3 was found decreased during stage evolution (FIGS. 3B-E). Localization of gal3 is interesting during stage evolution. In particular, stage I tumors showed a strong immunopositivity both in nucleus and cytoplasm (FIG. 3B), while in more advanced stages immunostaining was less intense and localized mainly in cytoplasm, with rare, occasional nucleus positivity (FIGS. 3C-E). The cytoplasmic localization of gal3 in higher stages of PCa is consistent with the anti-apoptotic behavior of cancer cells leading to drug resistance (13).

For TFD, strong expression was observed in stage II and III PCa (FIGS. 3H and I, respectively), while weak expression of TFD in stage I and IV PCa (FIGS. 3G and J, respectively) and no expression of TFD in normal prostate tissue (FIG. 3F) was noted. Overall, results indicated that TFD strongly expressed in stage II and III of PCa could participate with endothelial gal3 in tumor-endothelial cell interaction-step critical for metastasis. Expression of gal3 in early stages of PCa could be important for initiating tumor progression (11).

Figure 4:
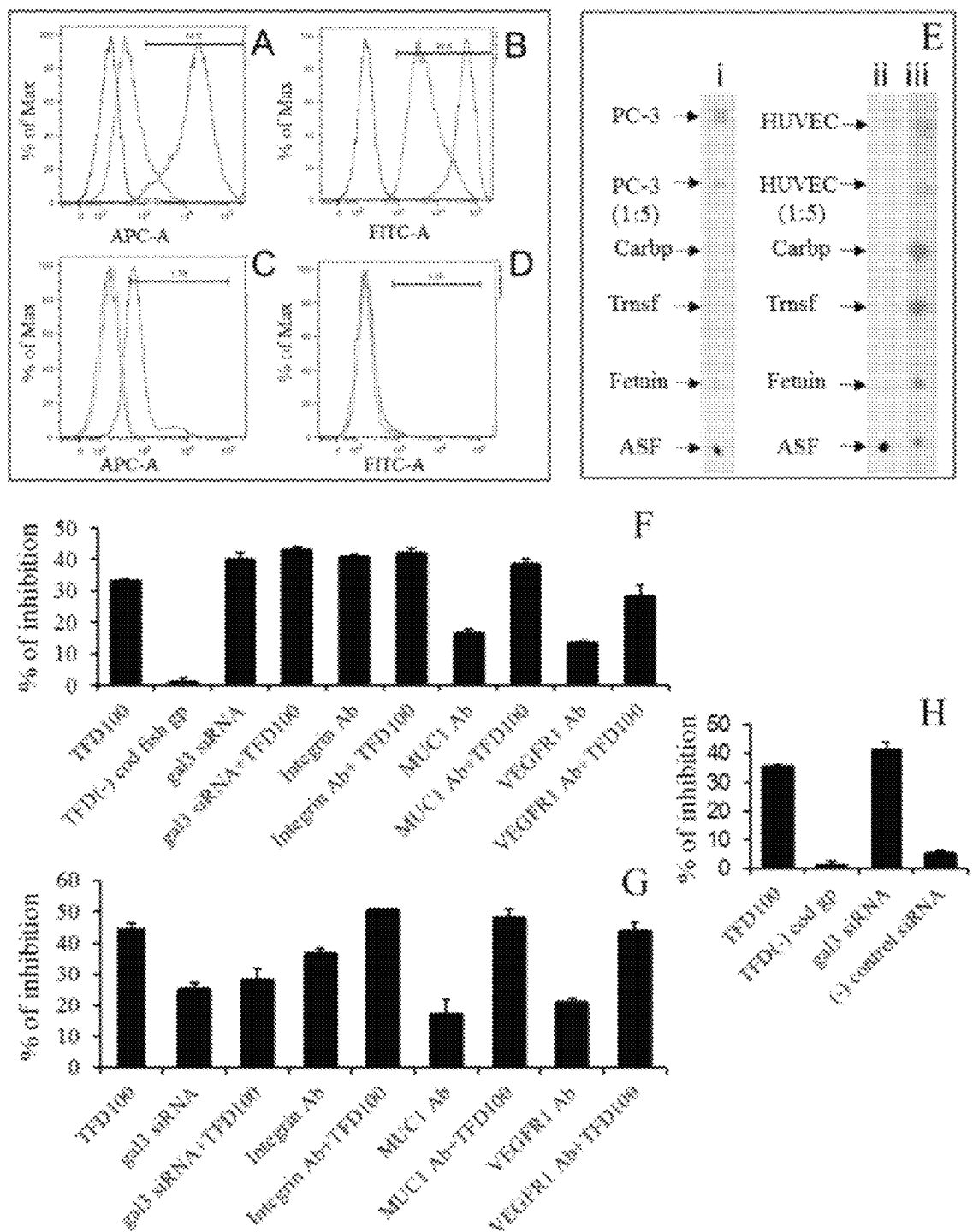
FIG. 4. Extracellular localization of gal3 and TFD in PC3 (FIGS. 4A, B) and HUVEC (FIGS. 4C, D) cells and adhesion of PC3 cells on HUVEC (FIGS. 4F-H). Expression of gal3 in PC3 (FIG. 4A) and HUVEC (FIG. 4C) cells.

For in vitro investigation of tumor-endothelial cell interactions, either labeled PC3 cells (with calcein) or HUVEC were pre-incubated with various reagents, washed and the labeled PC3 cells were allowed to interact with a monolayer of HUVEC cells. As a first step, expression of gal3 and TFD was investigated in both PC3 and HUVEC cells. PC3 cells were shown to express both gal3 (FIG. 4A) and TFD (FIG. 4B) on their surfaces as demonstrated by binding with anti-gal3 antibody and PNA, respectively on a flow cytometer. However, HUVEC cells express only gal3 (FIG. 4C), but not TFD (FIG. 4D) on their surfaces. The absence of TFD in HUVEC was confirmed with glycan differentiation analysis as PNA failed to bind with the HUVEC extract (FIG. 4E, ii). The expression of gal3 in PC3 and HUVEC are consistent with other studies (20, 21).

On tumor-endothelial cell interactions, the fluorescently labeled PC3 cells readily bound to HUVEC monolayer and the binding was inhibited by 33% when the PC3 cells were pre-treated with 3.5 nM $TFD_{100}$ (FIG. 4F). As expected, no inhibition of PC3-HUVEC interaction was observed (FIG. 4F) when PC3 cells were treated with 50 μg of TFD-negative fraction 4 (see Table 1). Consistent with this, PC3-HUVEC interaction was inhibited by 40% when gal3 was knocked down in PC3 cells using RNAi. The inhibition remained almost same when the PC3 cells were treated with both gal3 siRNA and $TFD_{100}$ suggesting that the $TFD_{100}$ is interacting primarily with the gal3 on the PC3 surface. To investigate other receptors that might be involved in PC3-HUVEC interactions, PC3 cells were pre-incubated with antibodies against integrin and MUC1 and 16-40% inhibition of tumor-endothelial cell interactions was observed. Co-incubation with antibody and $TFD_{100}$ increased inhibition of tumor-endothelial cell interactions suggesting that gal3-independent interaction was involved in that process.

When a HUVEC monolayer was pre-incubated with 3.5 nM $TFD_{100}$, tumor-endothelial cell interactions were inhibited by 45% (FIG. 4G). Similar to PC3, the inhibition of PC3-HUVEC interaction was more or less same when gal3 expression was knocked down in HUVEC using RNAi, or when combined with the $TFD_{100}$. This suggests that the $TFD_{100}$ is primarily interacting with the gal3 on the HUVEC surface. Similar to PC3, co-treatment of HUVEC monolayer with specific antibodies (such as integrin, MUC1, and VEGFR1) and $TFD_{100}$ increased inhibition of tumor-endothelial cell interactions suggesting that both gal3-dependent and gal3-independent interactions were involved in that process.

As gal3 is expressed in both PC3 and HUVEC, gal3 expression was knocked down in both cells using RNAi and performed tumor-endothelial cell interaction. Interestingly, gal3 siRNA treatment of both cells resulted inhibition (41%) as good as single treatment (FIG. 4H). Similarly, $TFD_{100}$ (3.5 nM) inhibited tumor-endothelial interaction by 34%. These results may suggest that gal3 is involved in trans interactions between PC3 and HUVEC. Overall, the results demonstrated efficacy of the $TFD_{100}$ to inhibit PC3-HUVEC interactions.

Figure 9:
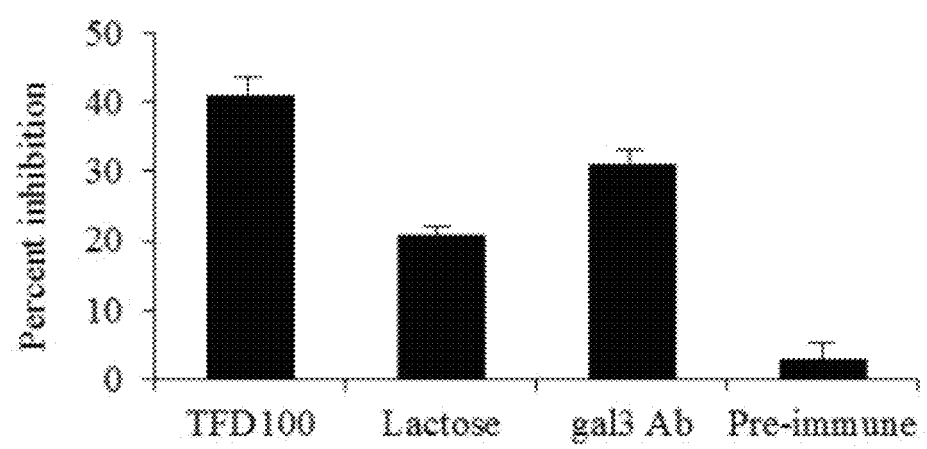
FIG. 9. MDA MB231 cell adhesion to HUVEC and its inhibition with TFD$_{100}$. All data are shown as the means±S.D. from three determinations. *, p<0.05, ANOVA.

The ability of $TFD_{100}$ to inhibit tumor-endothelial cell interaction was also investigated in a breast carcinoma model and $TFD_{100}$ was found to inhibit MDA MB231-HUVEC interactions by ~41% (FIG. 9).

Gal3-Induced Apoptosis of Human T Cells (MOLT-4, Jurkat, and $CD8^+$ T) and its Inhibition with $TFD_{100}$.

Figure 10:
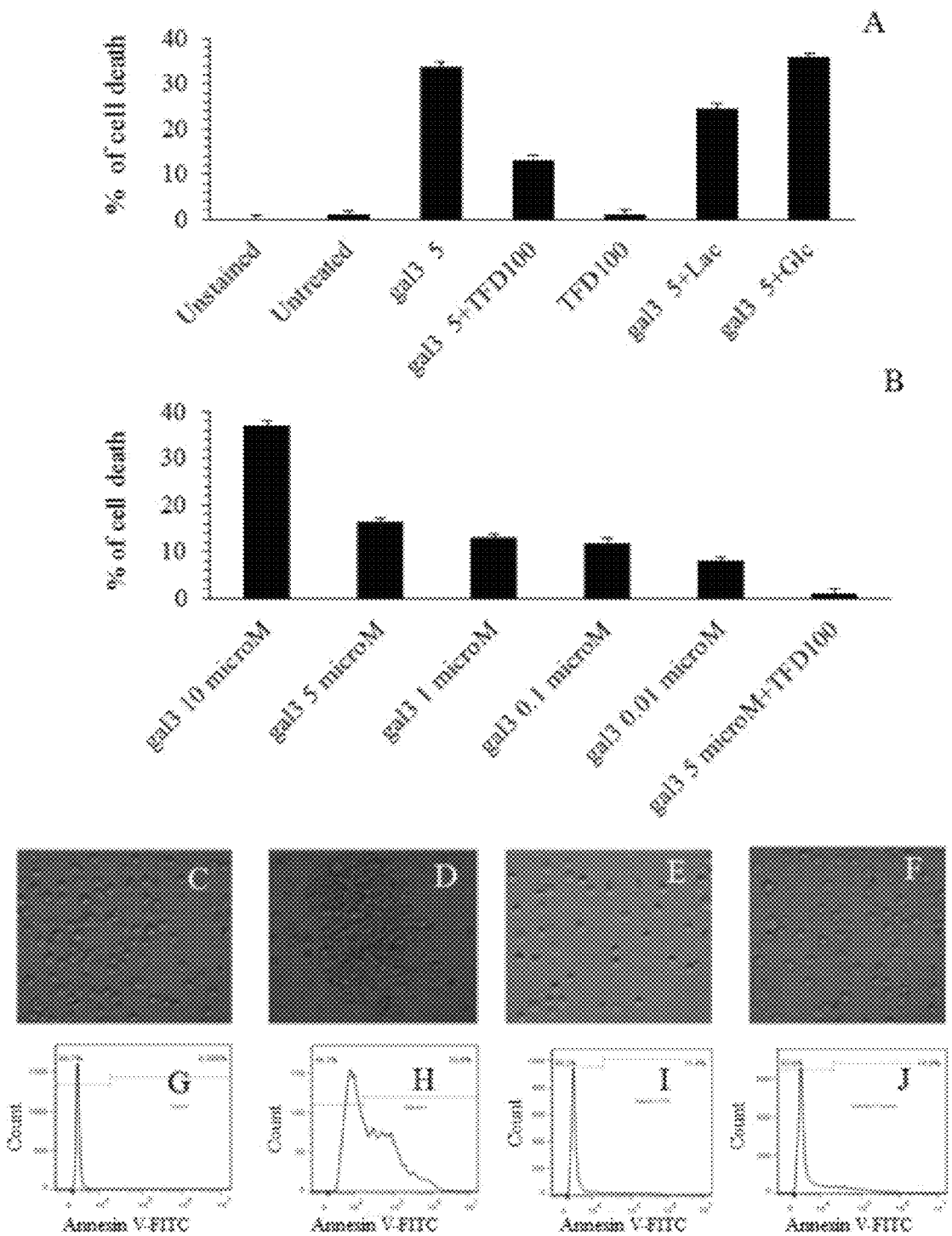
FIG. 10. Apoptosis of Jurkat (A,B) and human CD8+ (C-J) T cells.

Since most human cancer cells evade an immune response, the ability of $TFD_{100}$ to afford protection against tumor-induced apoptosis of T-cells was determined. The ability of $TFD_{100}$ to inhibit gal3-mediated apoptosis of human T cells was first examined. As shown in phase contrast microscopy, purified recombinant gal3 (5 μM) induced apoptosis of MOLT-4 cells through aggregation (FIG. 5B). Annexin V binding analyses showed that ~50% of MOLT-4 cells underwent apoptosis in presence of gal3 (FIG. 5F). This was inhibited by 34% in presence of 3.5 nM $TFD_{100}$ (FIG. 5C, G) or 50

µM lactose (~20% inhibition, FIG. 5D, H). Like MOLT-4, Jurkat cells underwent gal3 (5 µM)-mediated apoptosis (~34%), but was inhibited (~63%) by 3.5 nM of $TFD_{100}$. The gal3-mediated apoptosis was also significantly suppressed by a known inhibitor, lactose (~30% inhibition with 50 µM lactose) (FIG. 10A). In contrast, glucose (non-inhibitor of gal3) did not protect gal3-mediated apoptosis of Jurkat cells suggesting the gal3-mediated apoptosis was carbohydrate-dependent. To determine the minimum concentration of gal3 required to induce T-cell apoptosis, Jurkat cells were incubated with gal3 (10 nM to 10 µM) and cell death was assessed. A dose-dependent apoptosis was observed with the lowest concentration of gal3 (10 nM) causing ~8% apoptosis (FIG. 10B).

To investigate if gal3 can induce apoptosis of CD8+ cells, we isolated $CD8^+$ cells from peripheral blood mononuclear cells (PBMC) by depleting B cells, NK cells, monocytes, dendritic cells, $CD4^+$ T cells and granulocytes using a cocktail of antibodies and the CD8 T Cell Enrichment kit. The purity of $CD8^+$ cells was assessed on flow cytometry. Upon incubation with 5 µM gal3, $CD8^+$ cells underwent apoptosis as demonstrated by phase contrast microscopy (FIG. 10D) and flow cytometry (~54% cells death, FIG. 10H). This was blocked strongly by a pretreatment with either 3.5 nM $TFD_{100}$ (~77% inhibition, FIGS. 10E, I) or 50 µM lactose (~67% inhibition, FIGS. 10F, J).

Induction of Apoptosis of Tumor-Specific $CD8^+$ T Cells by Recombinant, Serum-Associated, and Tumor Cell-Associated Gal3 and its Inhibition with $TFD_{100}$.

To investigate if tumor-associated gal3 can induce tumor-specific $CD8^+$ T cell apoptosis, B16 melanoma-specific T cell transgenic D90.1 $CD8^+$ T cells (pmel T cells) (22) were studied. Following harvest of tumor-specific T cells from mouse spleen, a portion of the cells was activated with a peptide, allowed to proliferate in presence of IL-2, and investigated for apoptosis with recombinant gal3, patient serum-associated, and B16 tumor cell-associated gal3 at indicated time (FIG. 5I). Non-activated $CD8^+$ T cells at day 2 were also investigated for gal3-mediated apoptosis and they were insensitive to recombinant gal3 even up to 15 µM (~22% cell death in $CD8^+$ cells alone (FIG. 5K) or in the presence of gal3 (FIG. 5L)). However, apoptosis of activated $CD8^+$ T cells was induced with 5 µM recombinant gal3 (~76% (FIGS. 5O, Y) compared to CD8 alone (~61%, FIGS. 5N, Y), but was inhibited with 3.5 nM $TFD_{100}$ (~72%, FIGS. 5P, Y).

To investigate if patient serum-associated gal3 can induce apoptosis of CD8+ cells, prostate cancer patient serum was mixed with tumor-specific activated $CD8^+$ cells and apoptosis was measured. The prostate cancer patient sera (P17, P19) were found to contain more gal3 compared to normal serum (FIG. 5Q). Either patient serum induced apoptosis of tumor-specific $CD8^+$ cells (87-93%, FIGS. 5S, Y) compared to normal serum (~73%, FIGS. 5R, Y), and apoptosis was reduced to ~66% with 3.5 nM $TFD_{100}$ (FIGS. 5T, Y). The role of serum gal3 in induction of apoptosis was confirmed as gal3-depleted P19 serum showed reduced apoptosis (~87%) compared to the intact serum (~93%, FIG. 5Y).

B16 melanoma cells were confirmed to express gal3 on the surface (FIG. 5U). Upon incubation of activated tumor specific $CD8^+$ T cells on a monolayer of B16 cells for about 24 h, about 53% of T cells were found dead (FIGS. 5V, Z). $TFD_{100}$ (3.5 nM) reduced apoptosis of those T cells to 36% (FIGS. 5W, Z) and 39% with 50 µM lactose (FIG. 5Z). Similarly, human gal3 siRNA reduced apoptosis to 45% (FIGS. 5X, Z).

$TFD_{100}$ Inhibits Prostate Cancer Metastasis.

Figure 6:
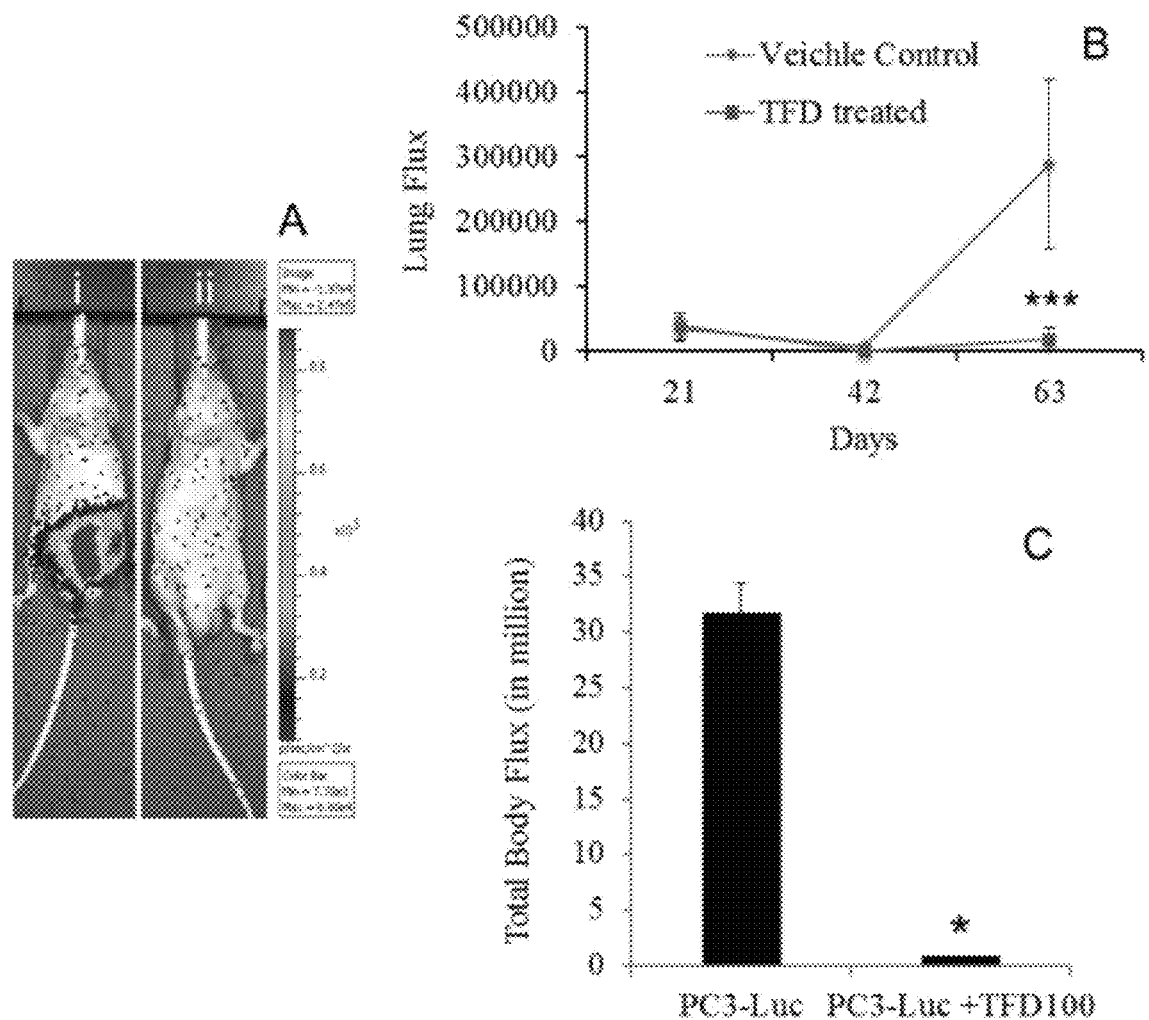
FIG. 6. Cancer metastasis induced by PC3-Luc cells and its inhibition with TFD$_{100}$.
Figure 11:
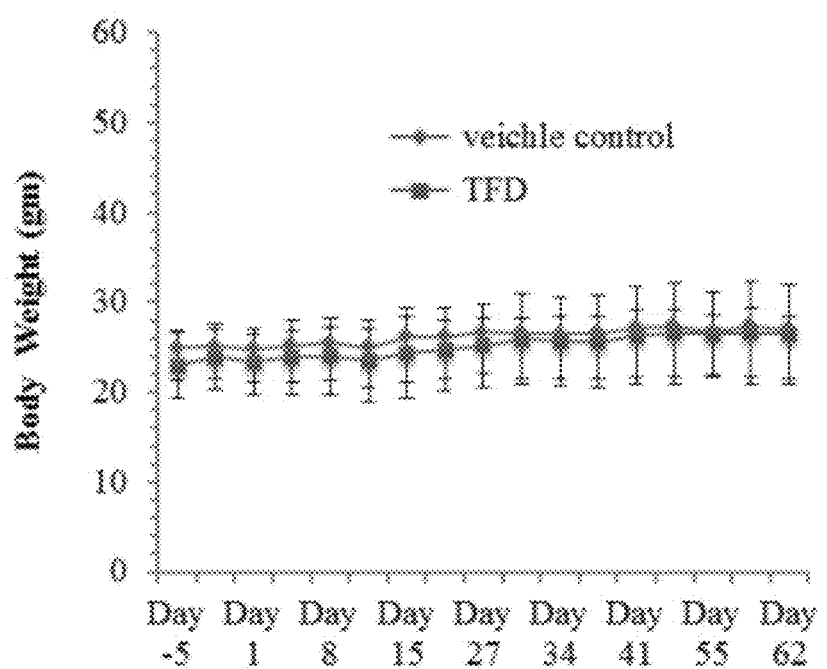
FIG. 11. Body weight of vehicle and TFD$_{100}$ treated mice.

Since PC3 cells express and secrete gal3, the effect of $TFD_{100}$ on formation of metastases was tested. Nude mice were administered with PC3 cells stably expressing a luciferase reporter. Tumor growth and motility in vivo was monitored using the Xenogen IVIS system for a period of 9 weeks. The control (vehicle treated) mice developed metastases in lower abdomen (FIG. 6A, i), but almost no metastasis in the treated $TFD_{100}$ group (FIG. 6A, ii). To investigate if there are any micro-metastases in lung, photons from lungs of both vehicle and $TFD_{100}$ treated mice were captured. Compared to vehicle treated mice, lung photon flux was markedly inhibited (~80%) in $TFD_{100}$ treated mice (FIG. 6B). Considering the whole body photon flux, the $TFD_{100}$ treated mice showed ~97% inhibition of tumor dissemination (FIG. 6C). The mouse body weight and serum chemistry related to the liver function for the treated group was unchanged when compared to the vehicle group (FIG. 11 and Table 3) suggesting that $TFD_{100}$ was not toxic to the animals.

TABLE 3

Serum chemistry of the $TFD_{100}$ treated mice

| Test | Result value | Normal range | Units |
| --- | --- | --- | --- |
| Albumin | 3.03 ± 0.05 | 2.5-4.6 | g/dL |
| Alanine aminotransferase | 51.33 ± 2.51 | 35-222 | U/L |
| Total Bilirubin | 0.1 ± 0.00 | 0.0-0.9 | mg/dL |
| Calcium | 10.83 ± 1.19 | 6.0-13.0 | mg/dL |
| Total Protein | 4.76 ± 0.20 | 3.9-6.4 | g/dL |
| Blood Urea Nitrogen | 23.33 ± 5.50 | 9-33 | mg/dL |

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1) Djeu J Y, Wei S (2000) Clusterin and chemoresistance. Adv Cancer Res 105:77-92.
2) Al-Mehdi A B et al (2000) Intravascular origin of metastasis from the proliferation of endothelium-attached tumor cells: a new model for metastasis. Nat Med 6:100-102.
3) Yu L G (2007) The oncofetal Thomsen-Friedenreich carbohydrate antigen in cancer progression. Glycoconj J 24: 411-420.
4) Glinsky V V et al (2001) The role of Thomsen-Friedenreich antigen in adhesion of human breast and prostate cancer cells to the endothelium. Cancer Res 61:4851-4857.
5) Zhao Q et al (2010) Interaction between circulating galectin-3 and cancer-associated MUC1 enhances tumour cell homotypic aggregation and prevents anoikis. Mol Cancer 9: 154-165.
6) Shekhar M P et al (2004) Alterations in galectin-3 expression and distribution correlate with breast cancer progression: functional analysis of galectin-3 in breast epithelial-endothelial interactions. American J Pathol 165:1931-1941.
7) Wu A M et al (2008) Differential contributions of recognition factors of two plant lectins—*Amaranthus caudatus* lectin and *Arachis hypogea* agglutinin, reacting with 7) Thomsen-Friedenreich disaccharide (Galbeta1-3GalNA-calpha1-Ser/Thr). Biochimie 90:1769-1780.
8) Ahmed H, Chatterjee B P (1989) Further characterization and immunochemical studies on the carbohydrate specificity of jackfruit (*Arthocarpus integrifolia*) lectin. J Biol Chem 264: 9365-9372.
9) Ideo H, Seko A, Yamashita K (2007) Recognition mechanism of galectin-4 for cholesterol 3-sulfate. J Biol Chem 282:21081-21089.
10) Nagae M et al (2006) Crystal structure of the galectin-9 N-terminal carbohydrate recognition domain from *Mus musculus* reveals the basic mechanism of carbohydrate recognition. J Biol Chem 281:35884-35893.
11) Liu F T, Rabinovich G A (2005) Galectins as modulators of tumour progression. Nat Rev Cancer 5:29-41.
12) Liao D I, Kapadia G, Ahmed H, Vasta G R, Herzberg O (1994) Structure of S-lectin, a developmentally regulated vertebrate β-galactoside binding protein. Proc Natl Acad Sci USA 91:1428-1432.
13) Fukumori T (2006) Galectin-3 regulates mitochondrial stability and antiapoptotic function in response to anticancer drug in prostate cancer. Cancer Res 66:3114-3119.
14) Nangia-Makker P, Balan V, Raz A (2008) Regulation of tumor progression by extracellular galectin-3. Cancer Microenviron 1:43-51.
15) Fukumori T et al (2003) CD29 and CD7 mediate galectin-3-induced type II T-cell apoptosis. Cancer Res 63:8302-8311.
16) Hsu D K, Chen H Y, Liu F T (2009) Galectin-3 regulates T-cell functions. Immunol Rev 230:114-127.
17) Li W, Jian-jun W, Xue-Feng Z, Feng Z (2010) CD133(+) human pulmonary adenocarcinoma cells induce apoptosis of CD8(+) T cells by highly expressed galectin-3. Clin Invest Med 33:E44-53.
18) DeVries A L, Vandenheede J, Feeney R E (1971) Primary structure of freezing point-depressing glycoproteins. J Biol Chem 6:305-308.
19) Fletcher G L, King M J, Kao M H (1987) Low temperature regulation of antifreeze glycopeptide levels in Atlantic cod (*Gadus morhua*). Can J Zool 65:227-233.
20) Pacis R A et al (2004) Decreased galectin-3 expression in prostate cancer. Prostate 44:118-123.
21) Ahmed H, Cappello F, Rodolico V, Vasta G R (2009) Evidence of heavy methylation in the galectin-3 promoter in early stages of prostate adenocarcinoma: Development and validation of a methylated marker for early diagnosis of prostate cancer. Translational Oncol 2:146-156.
22) Geng D et al (2010) Amplifying TLR-MyD88 signals within tumor-specific T cells enhances antitumor activity to suboptimal levels of weakly immunogenic tumor antigens. Cancer Res 70:7442-7454.
23) Massa S M, Cooper D N, Leffler H, Barondes S H (1993) L-29, an endogenous lectin, binds to glycoconjugate ligands with positive cooperativity. Biochemistry 32:260-267.
24) Ketis N V, Girdlestone J, Grant C W (1980) Positive cooperativity in a (dissected) lectin-membrane glycoprotein binding event. Proc Natl Acad Sci USA 77:3788-3790.
25) Carmeliet P, Jain R K (2000) Angiogenesis in cancer and other diseases. Nature 40:249-257.
26) Markowska A I, Liu F T, Panjwani N (2010) Galectin-3 is an important mediator of VEGF- and bFGF-mediated angiogenic response. J Exp Med 207:1981-1993.
27) Nangia-Makker P et al (2000) Galectin-3 induces endothelial cell morphogenesis and angiogenesis. Am J Pathol 156:899-909.
28) Springer G F (1997) Immunoreactive T and Tn epitopes in cancer diagnosis, prognosis, and immunotherapy. J Mol Med 75:594-602.
29) Almogren A et al (2012) Anti-Thomsen-Friedenreich-Ag (anti-TF-Ag) potential for cancer therapy. Front Biosci (Schol Ed) 4:840-863.
30) Lawrence M B, Springer T A (1991) Leukocytes roll on a selectin at physiologic flow rates: distinction from and prerequisite for adhesion through integrins. Cell 65:859-873.
31) Peng W, Wang H Y, Miyahara Y, Peng G, Wang R F (2008) Tumor-associated galectin-3 modulates the function of tumor-reactive T cells. Cancer Res 68:7228-7236.
32) Zou W (2005) Immunosuppressive networks in the tumour environment and their therapeutic relevance. Nat Rev Cancer 5:263-274.
33) Yu L G et al (2007) Galectin-3 interaction with Thomsen-Friedenreich disaccharide on cancer-associated MUC1 causes increased cancer cell endothelial adhesion. J Biol Chem 282:773-781.
34) Ahmed H, Cappello F, Rodolico V, Vasta G R (2009) Evidence of heavy methylation in the galectin-3 promoter in early stages of prostate adenocarcinoma: Development and validation of a methylated marker for early diagnosis of prostate cancer. Translational Oncol 2:146-156.
35) Dubois M, Giles K, Hamilton J K, Rebers P A, Smith F (1951) Colorimetric method for determination of sugar. Nature 168:167.
36) Laemmli U K, Favre M (1973) Maturation of the head of bacteriophage T4.1. DNA packaging events. J Mol Biol 80:575-599.
37) Ahmed H, Pohl J, Fink N E, Strobel F, Vasta G R (1996) The primary structure and carbohydrate specificity of a β-galactosyl-binding lectin from toad (*Bufo arenarum* Hensel) ovary reveal closer similarities to the mammalian galectin-1 than to the galectin from the clawed frog *Xenopus laevis*. J Biol Chem 271:33083-33094.
38) Glinsky V V et al (2001) The role of Thomsen-Friedenreich antigen in adhesion of human breast and prostate cancer cells to the endothelium. Cancer Res 61:4851-4857.
39) Li W, Jian-jun W, Xue-Feng Z, Feng Z (2010) CD133(+) human pulmonary adenocarcinoma cells induce apoptosis of CD8(+) T cells by highly expressed galectin-3. Clin Invest Med 33:E44-53.
40) Geng D et al (2010) Amplifying TLR-MyD88 signals within tumor-specific T cells enhances antitumor activity to suboptimal levels of weakly immunogenic tumor antigens. Cancer Res 70:7442-7454.
41) Alimirah F, Chen J, Basrawala Z, Xin H, Choubey D (2006) DU-145 and PC-3 human prostate cancer cell lines express androgen receptor: implications for the androgen receptor functions and regulation. FEBS Lett. 580 (9): 2294-300.
42) Pulukuri S M, Gondi C S, Lakka S S, et al. (2005) RNA interference-directed knockdown of urokinase plasminogen activator and urokinase plasminogen activator receptor inhibits prostate cancer cell invasion, survival, and tumorigenicity in vivo. J. Biol. Chem. 280 (43): 36529-40.

What is claimed is:

1. A method of suppressing metastasis in a subject comprising administering an effective amount of a TFD-containing glycopeptide to a subject having cancer, wherein the TFD-containing glycopeptide is $TFD_{100}$, thereby suppressing metastasis in a subject.

2. The method of claim 1, wherein the cancer is prostate cancer.

3. The method of claim 1, wherein a pharmaceutical formulation comprising from about 5 mg/kg to about 50 mg/kg of the TFD-containing glycopeptide to body weight is administered to the subject.

4. The method of claim 1, wherein the subject is a human.

\* \* \* \* \*